United States Patent
Blodgett et al.

(10) Patent No.: US 11,625,003 B2
(45) Date of Patent: Apr. 11, 2023

(54) COHERENT OPTICAL HOLOGRAPHIC IMAGING

(71) Applicant: The Johns Hopkins University, Baltimore, MD (US)

(72) Inventors: David W. Blodgett, Ellicott City, MD (US); Carissa L. Rodriguez, Laurel, MD (US); Austen T. Lefebvre, Lutherville-Timonium, MD (US); Eyal Bar-Kochba, Silver Spring, MD (US); Nicole E. Steiner, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 156 days.

(21) Appl. No.: 16/906,354

(22) Filed: Jun. 19, 2020

(65) Prior Publication Data

US 2020/0401081 A1   Dec. 24, 2020

Related U.S. Application Data

(60) Provisional application No. 62/863,303, filed on Jun. 19, 2019, provisional application No. 62/863,306, filed on Jun. 19, 2019.

(51) Int. Cl.
*G03H 1/04* (2006.01)
*G03H 1/22* (2006.01)
*G02B 27/10* (2006.01)
*G02B 13/22* (2006.01)

(52) U.S. Cl.
CPC ........... *G03H 1/2205* (2013.01); *G02B 13/22* (2013.01); *G02B 27/1006* (2013.01); *G03H 1/0443* (2013.01); *G03H 2001/0463* (2013.01); *G03H 2001/2207* (2013.01); *G03H 2222/20* (2013.01); *G03H 2222/45* (2013.01); *G03H 2226/02* (2013.01)

(58) Field of Classification Search
CPC ............... G03H 1/2205; G03H 1/0443; G03H 2001/2207; G03H 2222/20; G03H 2222/45; G02B 13/22; G02B 27/1006
USPC .................. 359/35, 11, 10, 1; 356/450, 457
See application file for complete search history.

(56) References Cited

U.S. PATENT DOCUMENTS

| | | | | |
|---|---|---|---|---|
| 3,834,786 A | * | 9/1974 | Carlsen | G03H 1/0406 359/24 |
| 5,465,147 A | * | 11/1995 | Swanson | A61B 1/00183 356/497 |
| 5,907,404 A | * | 5/1999 | Marron | G01J 9/02 356/489 |

(Continued)

*Primary Examiner* — Audrey Y Chang
(74) *Attorney, Agent, or Firm* — Sung T. Kim

(57) ABSTRACT

A holographic imaging system may include an optical source configured to output a source beam, a splitter configured to split the source beam into a reference beam and an object beam that is incident on a target to form a scattered object beam, and a pre-filter comprising a telecentric lens and a spatial filter. The pre-filter may be configured to receive the scattered object beam and filter diffuse light from the scattered object beam to form a filtered scattered object beam. The system may also include a combiner configured to combine the filtered scattered object beam with the reference beam to form an interference beam, and an imaging array configured to receive the interference beam and generate raw holographic data based on the interference beam.

17 Claims, 19 Drawing Sheets

(56) References Cited

U.S. PATENT DOCUMENTS

2006/0007512 A1* 1/2006 Kanesaka ............ G11B 7/0065
359/12
2008/0068608 A1* 3/2008 Hara .................. G01B 11/2433
356/394

* cited by examiner

COHERENT OPTICAL HOLOGRAPHIC IMAGING

CROSS-REFERENCE TO RELATED APPLICATIONS

This application claims the benefit of U.S. Provisional Patent Application No. 62/863,303, filed on Jun. 19, 2019, the entire contents of which are hereby incorporated herein by reference, and this application claims the benefit of U.S. Provisional Patent Application No. 62/863,306, filed on Jun. 19, 2019, the entire contents of which are hereby incorporated herein by reference.

TECHNICAL FIELD

Exemplary embodiments of the present disclosure generally relate to holographic imaging techniques, and more specifically relate to holographic imaging in connection with coherent optical imaging to enable medical imaging and other imaging applications.

BACKGROUND

Imaging systems are employed for many different purposes. However, conventional imaging systems for imaging tissue and other features internal to the body tend to be large and bulky and, thus, not easily portable. Further, the quality of the images generated by conventional imaging systems is insufficient to support a variety of applications. Conventional imaging systems may also have relatively high power consumption when operating. Due to the size, complexity, and power requirements of conventional imaging systems, such systems tend to be expensive to procure, operate, and maintain, while also being limited in application.

BRIEF SUMMARY OF SOME EXAMPLES

According to some example embodiments, a holographic imaging system is provided. The holographic imaging system may comprise an optical source configured to output a source beam and a splitter configured to split the source beam into a reference beam and an object beam. The object beam may be incident on a target to form a scattered object beam. The holographic imaging system may further comprise a pre-filter comprising a telecentric lens and a spatial filter. The pre-filter may be configured to receive the scattered object beam and filter diffuse light from the scattered object beam to form a filtered scattered object beam. The holographic imaging system may further comprise a combiner configured to combine the filtered scattered object beam with the reference beam to form an interference beam, and an imaging array configured to receive the interference beam and generate raw holographic data based on the interference beam.

According to some example embodiments, a method is provided. The method may comprise outputting a source beam from an optical source and splitting the source beam into a reference beam and an object beam. The object beam may be incident on a target to form a scattered object beam. The method may further comprise receiving the scattered object beam and filtering diffuse light from the scattered object beam via a telecentric lens and a spatial filter to form a filtered scattered object beam, combining the filtered scattered object beam with the reference beam to form an interference beam, and receiving the interference beam at an imaging array.

According to some example embodiments, an apparatus is provided. The apparatus may comprise a pre-filter comprising a telecentric lens and a spatial filter. The pre-filter may be configured to receive a scattered object beam from an interaction with a target and filter diffuse light from the scattered object beam to form a filtered scattered object beam. The apparatus may also comprise a combiner configured to combine the filtered scattered object beam with the reference beam to form an interference beam, and an imaging array configured to receive the interference beam and generate raw holographic data based on the interference beam.

BRIEF DESCRIPTION OF THE SEVERAL VIEWS OF THE DRAWING(S)

Having thus described some example embodiments in general terms, reference will now be made to the accompanying drawings, which are not necessarily drawn to scale, and wherein:

DETAILED DESCRIPTION

Figure 1:
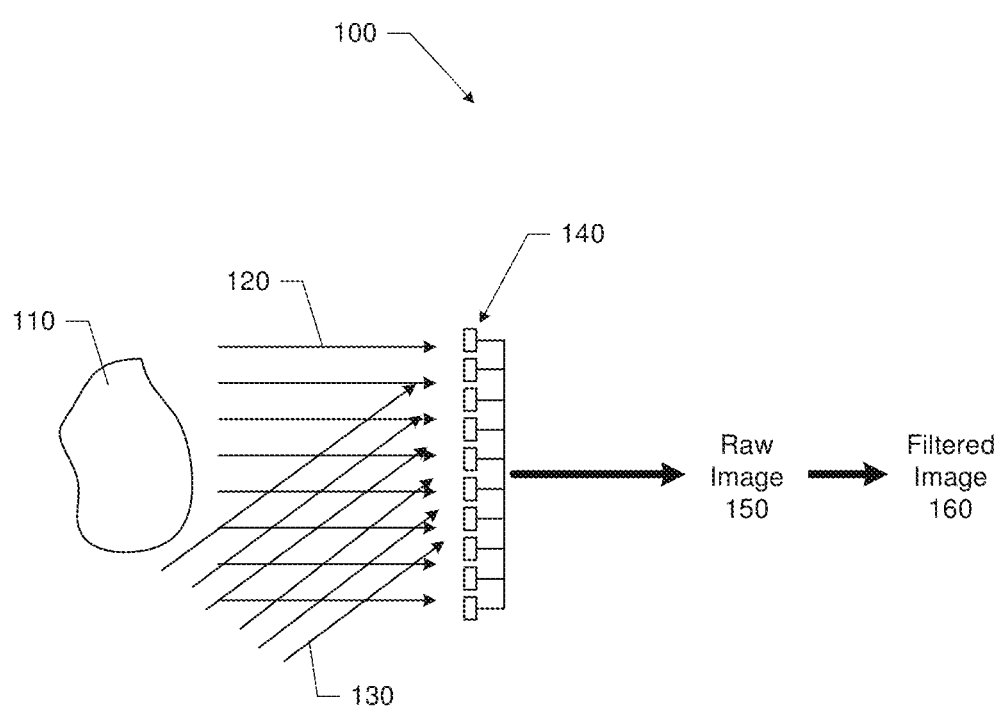
FIG. 1 illustrates a conceptual holographic imaging system according to some example embodiments.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

As used herein, the terms "component," "module," and the like are intended to include a computer-related entity, such as but not limited to hardware, firmware, or a combination of hardware and software. For example, a component or module may be, but is not limited to being, a process running on a processor, a processor, an object, an executable, a thread of execution, and/or a computer. By way of example, both an application running on a computing device and/or the computing device can be a component or module. One or more components or modules can reside within a process and/or thread of execution and a component/module may be localized on one computer and/or distributed between two or more computers. In addition, these components can execute from various computer readable media having various data structures stored thereon. The components may communicate by way of local and/or remote processes such as in accordance with a signal having one or more data packets, such as data from one component/module interacting with another component/module in a local system, distributed system, and/or across a network such as the Internet with other systems by way of the signal. Each respective component/module may perform one or more functions that will be described in greater detail herein. However, it should be appreciated that although this example is described in terms of separate modules corresponding to various functions performed, some examples may not necessarily utilize modular architectures for employment of the respective different functions. Thus, for example, code may be shared between different modules, or the processing circuitry itself may be configured to perform all of the functions described as being associated with the components/modules described herein. Furthermore, in the context of this disclosure, the term "module" should not be understood as a nonce word to identify any generic means for performing functionalities of the respective modules. Instead, the term "module" should be understood to be a modular component that is specifically configured in, or can be operably coupled to, the processing circuitry to modify the behavior and/or capability of the processing circuitry based on the hardware and/or software that is added to or otherwise operably coupled to the processing circuitry to configure the processing circuitry accordingly.

Holographic imaging is an approach to imaging that can be thought of as a lens-less imaging modality. In conventional imaging, ambient light scattered off of an object is collected by a lens and then imaged onto an array. The focal length of the lens can dictate the distance at which the objects are brought into focus. Conversely, in holographic imaging, the object is actively illuminated by a coherent light source, and the scattered light reflected from (or transmitted through) the object in the form of an object beam is constructively interfered with a reference beam (e.g., via a local oscillator) to form a hologram. The constructive interference of the object and reference beams allows for both magnitude and phase information about signals reflected from the object to be measured and recorded. Reconstruction of an image of the targeted object may occur through post-processing of a hologram using the magnitude and phase information, in effect creating a digital lens. Such a digital lens allows for images of objects to be generated at many or all viewpoints that can be reconstructed from a single hologram.

Coherent Holography Example

FIG. 1 illustrates a holographic imaging system 100 according to an example embodiment that utilizes a holographic imaging technique in which the object 110 (which may also be referred to as a target) is imaged at an imaging array 140 based on scattered light 120 reflected from the object 110. The imaging array 140 may be constructed of a plurality of light sensors assembled, for example, in a grid pattern. The scattered light 120 (also referred to as a scattered object beam or a scattered object wave) may be constructively interfered with by reference light 130 (also referred to as a reference beam or a reference wave). Both the scattered light 120 (prior to being reflected from the object 110) and the reference light 130 may originate from a coherent light source. A raw image 150 may be captured by the array 140 in the form of measurements at each sensor within the array 140. The measurements may be used to determine both magnitude (also referred to as intensity) and phase information that is imparted into the light received at the array 140 by the scattering caused by the object 110. Based on the raw image 150, a filtered image 160 may be generated using image processing techniques such as, for example, discrete Fourier transform (DFT) of the raw holographic data provided by the array 140. In this manner, holographic imaging may be performed as a coherent optics-based approach that optically filters diffuse photons to achieve a diffraction-limited resolution image in scattering mediums (e.g., the object 110).

Some example embodiments may enable the provision of a system capable of employing holographic imaging techniques that can be utilized, for example, for tissue and other medical imaging to detect changes in the tissue (e.g., motion) or even neural signatures within active neural tissue (which may be indicated by detected motion). Based on the wavelength of the light used, the light may penetrate into the body to detect internal neural and physiological activity. The use of coherent optics and holographic imaging can also provide high quality imaging without the bulk and physical optics that are necessary in conventional optical imaging systems. Such holographic imaging techniques can be used in the context of, for example, a brain to computer interface (BCI). Further, such holographic imaging techniques may be used in the context of other applications due to an ability to perform imaging using small components that can capture and analyze images at a very high rate, e.g., real-time. The ability to perform high speed, quality imaging creates the foundation upon which to implement a variety of applications that may be realized via holographic imaging techniques, but also requires that unique technical problems be solved to support such high-speed, high-quality imaging using relatively small sensors. Due to the small size of the sensors, holographic imaging systems may be constructed to allow for mobility of an individual while simultaneously imaging the individual's body (e.g., brain). Sensors may be placed external to the body, or even internal to the body due to their small size.

While holographic imaging may be realized by, for example, the high-level approach described with regard to FIG. 1, in order to develop increasingly high-quality images and identify small changes in images of a target over time (e.g., changes in neural or physiological activity within the body), improved optical hardware systems and post-processing techniques may be employed according to various example embodiments provided herein. For example, as further described herein, tissue motion that occurs after a trauma can be measured with a high sensitivity using such improved optical hardware systems and post-processing techniques according to various example embodiments provided herein. In many conventional imaging systems that solely rely on magnitude measurements, motion sensitivity is determined with the spatial resolution with the minimum detectable motion being on the order of one tenth to one half of the spatial resolution of the system. However, using phase-based measurements, which can be obtained via example embodiments of the holographic imaging systems described herein, motion sensitivity, for example, in an axial direction, can be determined as a function of the optical wavelength, thereby leading to 10×, 100×, or even 1000× improvements in sensitivity (e.g., from tens of microns to tens of nanometers). As such, according to some example embodiments, sub-micron motion can be detected and imaged accurately with repeatability, which can be a requirement for many tissue measurement applications. As such, via implementation of various aspects of the example embodiments described herein, improved holographic imaging can be realized, thereby giving rise to numerous new applications for holographic imaging that were previously unavailable.

Example Holographic Imaging Systems

Following from some of the holographic imaging techniques described above, FIG. 2 illustrates a block diagram of an example holographic imaging system 200, according to some example embodiments. The holographic imaging system 200, according to some example embodiments, may be modified in accordance with various example optimizations described herein to, for example, change or improve the operation of the holographic imaging system 200 and the resultant images and other outputs generated by the holographic imaging system 200, or to otherwise configure the holographic imaging system 200 for a specific application. As such, the holographic imaging system 200 provides, according to some example embodiments, a foundational building block upon which various example embodiments described herein may be constructed and implemented.

The holographic imaging system 200 may comprise optical hardware 210 configured to cause light to interact with a target 290 (or object) to generate raw holographic data of the target 290 for provision to the image data processor 270 for post-processing and analysis according to various example embodiments. According to various example embodiments, the target 290, as further described herein with respect to various applications, may be any substance or matter that is desired to be imaged. According to some example embodiments, the target 290 may be a scattering medium such as biologic tissue as further described herein. The optical hardware 210 involved in imaging the target 290 may be constructed and organized in a variety of ways. However, the optical hardware 210 may be generally configured to form an interference beam 258 by combining or mixing a scattered object beam 256, which has interacted with the target 290, with a reference beam 252, and converting the interference beam 258 into raw holographic data by an imaging array 220 for analysis. According to some example embodiments, the optical hardware 210 may comprise an imaging array 220, an array controller 225, an optical source 230, a splitter 235, and a combiner 240. These components, with the assistance of some additional, passive optical components that are not shown in FIG. 2, may be organized into a system having a reflection configuration or a transmission configuration. The holographic imaging system 200 is constructed in a reflection configuration where the scattered object beam 256 is a reflection of light from the target 290. However, as described below with respect to FIG. 4, a holographic imaging system 201 may be constructed using similar components in a transmission configuration where the scattered object beam 256 is formed by the object beam 254 transmitting through the target 290.

The optical source 230 may be a light source for the holographic imaging system 200 and thus may be configured to generate a source beam 250. For example, according to some example embodiments, the optical source 230 may be a laser configured to output coherent light (e.g., spatially coherent or temporally coherent) as the source beam 250. Additionally, the optical source 230 may be configured to have a given coherence length, i.e., a length or distance over which the source beam 250 maintains a threshold degree of coherence. In this regard, for example, a long coherence length source may have a coherence length that is greater than ten meters, while a short coherence length source may have a coherence length of less than five millimeters. The optical source 230 may be selected to have any coherence length, often depending upon the application. According to some example embodiments, short coherence length optical sources (e.g., five millimeters or between two and ten millimeters) may be utilized. According to some example embodiments, the optical source 230 may comprise a local oscillator that may generate a signal frequency used to generate a frequency and wavelength of the source beam 250. According to some example embodiments, a wavelength of the source beam 250 output by the optical source 230 may be selected to be any optical wavelength, often depending on the application, such as, for example, wavelengths from 780 nanometers to 1310 nanometers. As a laser source, the optical source 230 may include, for example, a laser diode driver configured to generate photons via a P-material and N-material junction. Further, the optical source 230 may be configured to control various aspects of the source beam 250 to provide a desired output. In this regard, the optical source 230 may perform optical filtering to generate the source beam 250. According to some example embodiments, the optical source 230 may include temperature control devices, such as, for example a thermoelectric cooler (TEC) to control a temperature of the optical source 230 to maintain the source beam 250 within a desired quality range with respect to frequency and scattering characteristics.

The source beam 250 generated by the optical source 230 may be provided to components of the optical hardware 210 to generate the reference beam 252 and the object beam 254. In this regard, according to some example embodiments, the source beam 250 may be provided to a splitter 235 that is configured to separate the source beam 250 into the reference beam 252 and the object beam 254. The splitter 235 may be a passive optical device that can be configured to split an input beam into two output beams, i.e., the reference beam 252 and the object beam 254, that exit the splitter 235 in different directions. According to some example embodiments, the splitter 235 may comprise, for example, two triangular glass prisms affixed together with a resin. According to some example embodiments, the splitter 235 may be a half-silvered mirror with a transparent, thin coating of metal (e.g., aluminum) or a dichroic optical coating.

Further, according to some example embodiments, the splitter 235 may be a polarizing beam splitter that outputs the reference beam 252 and the object beam 254 such that the beams are orthogonally polarized relative to each other. As a polarizing beam splitter, the splitter 235 may control the relative amount of light in the object beam 254 and reference beam 252 through rotation of the polarization of the optical beam incident on the splitter 235 (i.e., the source beam 250). According to some example embodiments, the splitter 235, operating as a polarizing beam splitter, may be selected to provide, for example, more optical power to the object beam 254, relative the optical power provided to the reference beam 252, to increase or maximize the amount of detected scattered light from the target 290. Alternatively, the splitter 235 may be a fixed beam splitter (e.g., having an optical power ratio parameter such as 50:50 or 90:10 ratio for the object beam 254 and the reference beam 252, respectively). Additionally, or alternatively, the object beam 254 or the reference beam 252 may be subjected to a phase or frequency shift upon exiting the splitter 235. In this regard, for example, depending on the design of the holographic imaging system 200, a shift device may be included that is configured to introduce a frequency or phase shift into the object beam 254 or the reference beam 252 to allow for heterodyne processing of the raw holographic data generated by the imaging array 220.

As mentioned above, the object beam 254 interacts with the target 290 to impart information about the target 290 into, for example, the scattered object beam 256 that is reflected from the target 290 due to exposure to the object beam 254. The reference beam 252, on the other hand, may remain internal to the holographic imaging system 200. In this regard, the reference beam 252 does not interact with the target 290 and is maintained in a pristine state until the reference beam 252 is mixed with the scattered object beam 256, for example, at a combiner 240.

In this regard, the scattered object beam 256 and the reference beam 252 may be received by the combiner 240, and the combiner 240 may be configured to combine or mix the scattered object beam 256 with the reference beam 252 to form an interference beam 258. Similar to the splitter 235, the combiner 240 may be a passive optical device. The combiner 240 may be configured to receive two input beams and output a single beam that is a mixture of the two input beams. As such, the combiner 240 may simply operate as a reverse splitter and may be constructed in the same or similar manner as the splitter 235, other than to be oriented to receive two input beams and provide one output beam. As such, the combiner 240 may comprise, for example, two triangular glass prisms affixed together with a resin. According to some example embodiments, the combiner 240 may be a half-silvered mirror with a transparent, thin coating of metal (e.g., aluminum) or a dichroic optical coating. Further, according to some example embodiments, the combiner 240 may be a polarizing beam combiner that receives two orthogonally polarized input beams and mixes the two input beams to generate an output beam at a single polarization using a polarizer located at the output of the combiner.

According to some example embodiments, since the source beam 250 is a coherent source, the mixing of the scattered object beam 256 with the reference beam 252 by the combiner 240 may cause constructive or destructive interference between the beams within the combiner 240. As a result, the interference beam 258 provided as an output of the combiner 240 may capture changes in the object beam 254 that occurred due to interaction with the target 290. Therefore, the interference beam 258 may include magnitude and phase information that can be used to form an image, e.g., a complex image, of the target 290.

Accordingly, the interference beam 258 may be received by the imaging array 220, which may be configured to convert the interference beam 258, and the information about the target 290 included in the interference beam 258, into raw holographic data. In this regard, the imaging array 220 may be a focal plane array for the optical hardware 210 of the holographic imaging system 200. The imaging array 220 may be formed of a collection of optical sensors in the form of, for example, photoreceivers. According to some example embodiments, the optical sensors may be assembled in a grid pattern. Measurements of the light received at each optical sensor within the imaging array 220 may be taken and converted into raw holographic data. The measurements may include information in the form of both magnitude and phase information that is imparted into the scattered object beam 256, and thus in turn the interference beam 258 received at the imaging array 220.

The operation of the imaging array 220 may be controlled by an array controller 225 that is operably coupled to the imaging array 220. The array controller 225 may comprise processing circuitry that may be configured via hardware or software to cause the imaging array 220 to implement various functionalities as descried herein. According to some example embodiments, the array controller 225 and the imaging array 220 may be components of an imaging array assembly. The array controller 225 may be configured to control a variety of different parameters of the imaging array 220, such as, for example, the frame rate, capture timing, or the integration time of the imaging array 220. The frame rate may be a speed (e.g., in frames per second) at which the imaging array 220 performs successive capture operations (i.e., capture events) on the interference beam 258, thereby generating successive frames of data, each at a different time, for analysis.

Controlling the capture timing parameter of the imaging array 220 may include controlling the timing of the initiation of a capture event. According to some example embodiments, a capture event may include the process of collecting a measurement of the received light at the imaging array 220 (i.e., a frame of received light), generating associated data for the received light (i.e., a frame of raw holographic data), and preparing to capture a subsequent measurement of received light. The duration of this process may be referred to as the integration time for the imaging array 220, as further described below. The timing of the initiation of the capture event may be controlled by the array controller 225. In this regard, according to some example embodiments, the array controller 225 may be configured to coordinate or synchronize the initiation of a capture event with, for example, the optical source 230 to implement certain functionalities as further described herein. Additionally, according to some example embodiments, the array controller 225 may be configured to coordinate or synchronize the initiation of a capture event with other components of the system 200, such as, for example, optical switches or the like. According to some example embodiments, the system 200 may include one or more optical switches to facilitate operation of a mechanical shutter for the imaging array 220. The optical switches may be high-speed switches implemented, for example, as microelectromechanical systems (MEMS) devices for operation as a mechanical shutter. As MEMS devices, such optical switches may have a less than one millisecond actuation speed. As semiconductor devices, such optical switches may have a less than one nanosecond actuation speed.

Additionally, according to some example embodiments, the imaging array 220 may be configured to capture light incident upon the imaging array 220 in accordance with an integration time. In this regard, the integration time of the imaging array 220, which may be a parameter of the imaging array 220 that is controlled the array controller 225, may be the duration of time to complete a capture event as described above and otherwise herein.

Under the control of the array controller 225, the imaging array 220 may be configured to provide the raw holographic data generated by the imaging array 220 to the image data processor 270. The image data processor 270, as further described below, may comprise processing circuitry that may be configured via hardware or software to perform post-processing of the raw holographic data received from the imaging array 220, followed by image processing to form an image. The image data processor 270, for example, may be configured to receive the raw holographic data from the imaging array 220 or the array controller 225. The raw holographic data may represent the intensity measurements of the interference beam 258 received at the imaging array 220 (i.e., after the scattered object beam 256 and the reference beam 252 have been coherently mixed). The image data processor 270 may be configured to generate a complex image from the raw holographic data. To do so, according to some example embodiments, the image data processor 270 may be configured to apply the raw holographic data to a Fresnel transform, perform a convolution, and utilize angular spectrum processing to convert the raw holographic data into a complex image. Regardless of the technique used to generate the complex image, according to some example embodiments, the complex image may comprise both magnitude and phase information corresponding to the target 290.

Figure 3:
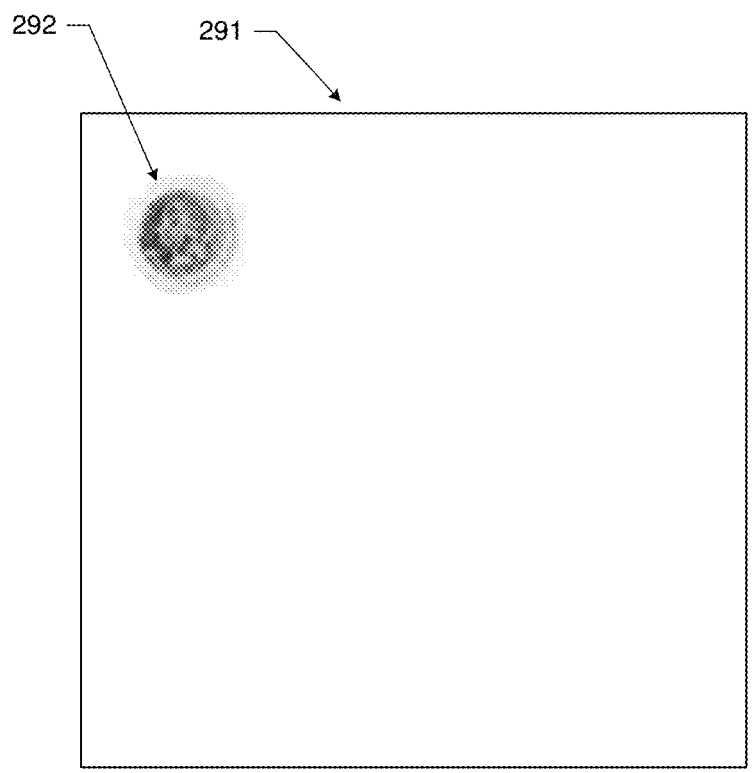
FIG. 3 illustrates a rendering of an image based on a frame of data according to some example embodiments.

In this regard, for example, FIG. 3 illustrates according to an example embodiment a rendering of a frame 291 of the target 290 in the form of an image 292 after, for example, post-processing of the raw holographic data and image processing, as further described herein. In this regard, a variety of post-processing and image processing techniques may be employed to improve the image quality and allow for high-value analysis of the images generated from the raw holographic data.

Figure 4:
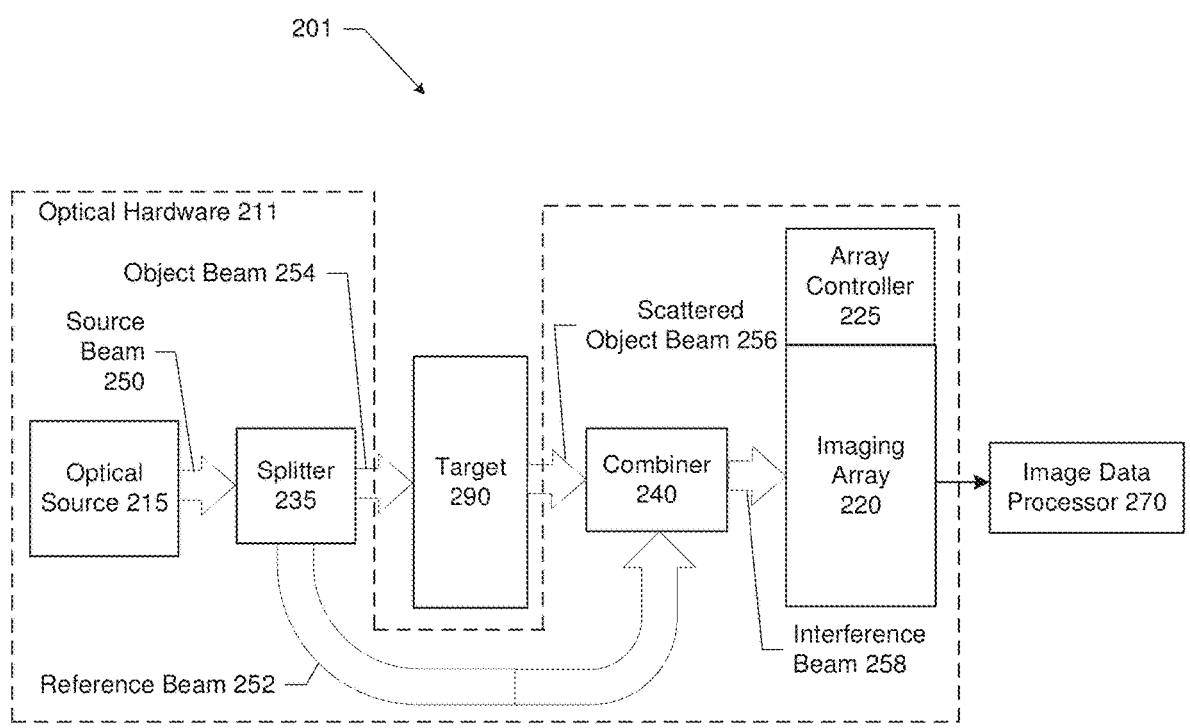
FIG. 4 illustrates a block diagram of a holographic imaging system in a transmission configuration according to some example embodiments.

As mentioned above, the holographic imaging system 200 may be constructed in a reflection configuration where the scattered object beam 256 is formed as a reflection of light from the target 290. Now referring to FIG. 4, a block diagram of a holographic imaging system 201 according to an embodiment is shown comprising optical hardware 211 that may be constructed using the same or similar components as the optical hardware 210, but assembled in a transmission configuration where the scattered object beam 256 is formed by the object beam 254 being transmitted through the target 290. As shown in FIG. 4, rather than being received by the combiner 240 as a reflection from the target 290, the scattered object beam 256 is received as a transmission through the target 290. As such, the target 290 is disposed between the splitter 235 and the combiner 240. Other than these structural changes, the individual components and the overall holographic imaging system 201 operate in the same or similar manner as the holographic imaging system 200, particularly with respect to generation of the interference beam 258 for receipt by the imaging array 220. As such, one of skill in the art would appreciate that, while various example embodiments described herein may be described with respect to a holographic imaging system that is constructed in a reflection configuration, the example embodiments would also be applicable to holographic imaging systems constructed in a transmission configuration.

Having described the holographic imaging system 200 as a foundation for incorporating various improvements and optimizations described herein, various optical hardware-based improvements and optimizations will now be described. In this regard, improvements and optimizations in the form of additional or reconfigured components may be implemented, or improvements and optimizations with regard to the control of, for example, the imaging array 220 by the array controller 225 may be implemented. In this regard, by way of introduction, the optical hardware of a holographic imaging system may include a telecentric lens operating in association with a spatial filter for Fourier filtering of diffuse photons and to allow for increased distances between the imaging array and the target to be imaged. Further, according to some example embodiments, the optical hardware may include a second reference arm (as shown, for example, in FIG. 11) that generates a second reference beam at a different angle from the first reference beam to permit capture of multiple images, which can be later decomposed in post-processing, in a single frame capture. With respect to control of the optical hardware, a number of optimization techniques may be employed in the optical hardware that, in some cases, may be linked to post-processing techniques to improve image capture and quality. In this regard, for example, the frame rate for image capture may be controlled in accordance with a decorrelation time for the type of target or object. By triggering image captures at a rate faster than the decorrelation time of the target (e.g., tissue), noise, such as optical phase noise, can be more readily identified and removed from a series of images to generate a more detailed image with higher contrast. Further, the optical source may be controlled to output light at a desired wavelength for the type of targeted object, because different types of target objects may provide more or less backscatter or may be more easily imaged through at certain wavelengths. Therefore, according to some example embodiments, the wavelength may be tuned, via control of the optical source, to output a desired wavelength. Additionally, as mentioned above with respect to the provision of a second reference beam at a different angle, the optical source and the imaging array may be controlled to cause a second image capture at a different time during a single frame capture. In this regard, such a technique may be implemented, for example, in situations where the decorrelation time is shorter than a maximum frame rate (time between frames) of the imaging array 220, but longer than a minimum time between two images being captured during a single frame capture event.

Accordingly, with respect to hardware-based improvements and optimizations, for example, the holographic imaging system 200 may be modified to include a beam angle separator that acts upon the object beam 254 prior to being incident upon the target 290. The inclusion of a beam angle separator can provide for imaging at different depths within the target 290. To do so, for example, the beam angle separator may split the object beam 254 into multiple beams, for example, in association with a number of windows of the beam angle separator, as described in U.S. Pat. No. 10,413,186, entitled "Coherent Optical Imaging for Detecting Neural Signatures and Medical Imaging Applications Using Holographic Imaging Techniques," which is incorporated herein in its entirety. Accordingly, through use of such a beam angle separator, or other techniques, imaging at different depths may be implemented as a variation to the holographic imaging system 200.

Example Pre-Filtering

Figure 5:
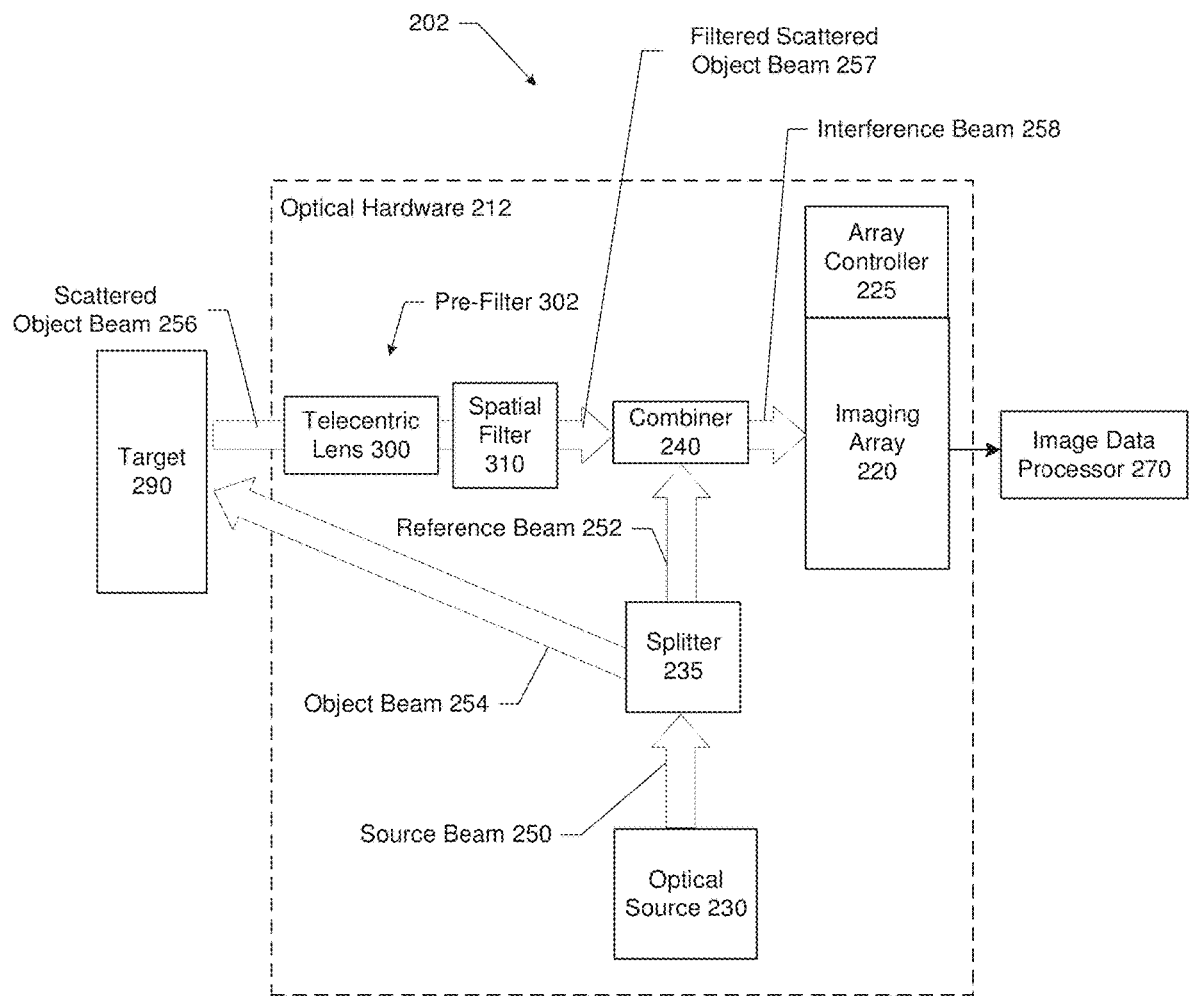
FIG. 5 illustrates a block diagram of a holographic imaging system with pre-filtering according to some example embodiments.
Figure 7:
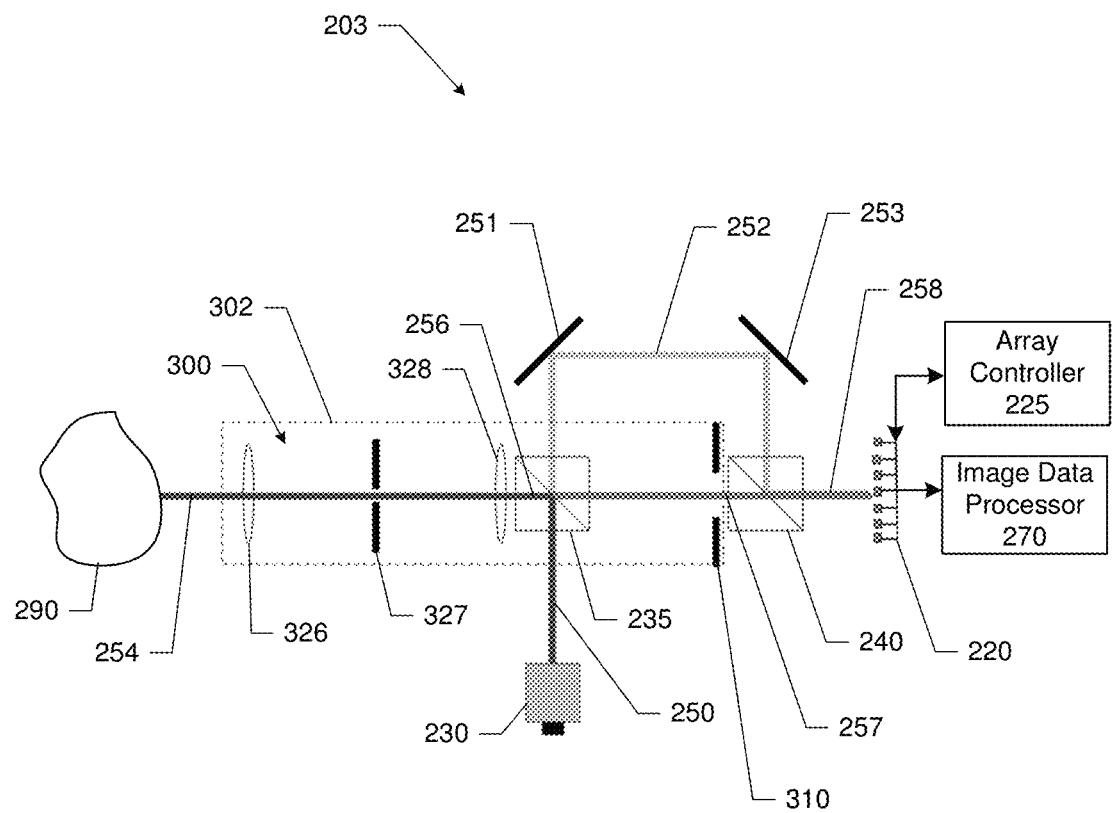
FIG. 7 illustrates an optical schematic of a holographic imaging system with pre-filtering according to some example embodiments.

With reference to FIG. 5, a holographic imaging system 202 according to an embodiment is shown that builds upon of the holographic imaging system 200, and includes a variation to the optical hardware 210 in the form of optical hardware 212. Optical hardware 212, according to some example embodiments, may include additional hardware components that perform pre-filtering of the scattered object beam 256 before being mixed with the reference beam 252 and provided to the imaging array 220 as the interference beam 258. In this regard, according to some example embodiments, the optical hardware 212 may further comprise a pre-filter 302 comprising a telecentric lens 300 with a Fourier filter placed at the Fourier plane behind a first lens in the telecentric lens, which may then be followed by a spatial filter 310 located at the image plane. The pre-filter 302 may, therefore, be configured to receive and filter the scattered object beam 256 to form a filtered scattered object beam 257 for use in mixing with the reference beam 252 by the combiner 240 to generate the interference beam 258. According to some example embodiments, the object beam 254 may be incident upon the target 290 via an off-axis configuration (as shown in FIG. 5), which permits the object beam 254 to be incident upon the target 290 without passing through the pre-filter 302. According to some example embodiments that use an on-axis configuration, the object beam 254 may pass through the pre-filter 302 (as shown in FIG. 7). However, in such an on-axis configuration, the pre-filter 320 may operate to permit the object beam 254 to pass through the pre-filter 320, prior to being incident upon the target 290, substantially unaffected. In some instances, a benefit of an on-axis configuration may be that the system can allow for more compact configurations and therefore smaller system constructions. Regardless of whether an off-axis or an on-axis configuration is used, the scattered object beam 256 may pass through the pre-filter 302.

The telecentric lens 300 of the pre-filter 302 may comprise a number of lenses, e.g., lenses 326 and 328 as further described below, and a spatial Fourier filter 327. The spatial filter 310 may be placed in association with the lenses of the telecentric lens 300. The pre-filter 302 may be positioned within the optical hardware 212 between the target 290 and the combiner 240 to act upon the scattered object beam 256. However, according to some example embodiments, the pre-filter 302 may be positioned to act upon the interference beam 258 after mixing of the scattered object beam 256 with the reference beam 252 to form a filtered interference beam in the same or similar manner as described with respect to the scattered object beam 256. According to some example embodiments, the telecentric lens 300 may operate to enable increased distances (on the order of, for example, 110 millimeters) between the optical hardware 212 and the target 290, and also condition the scattered object beam 256 for further filtering via the spatial filter 310, prior to being combined with the reference beam 252 in the combiner 240. To do so, the telecentric lens 300 may have a relatively large focal length and large diameter lenses to collect the light scattered from the target 290 at the same scatter angles as when the target 290 is placed closer to the telecentric lens 300 and in front of the imaging array 220. For example, a system operating with a source beam 250 at a 780 nanometer wavelength, with a 1024×1024 pixel imaging array 220 having 5 micron pixels may be limited to about 5 degrees of scattered light to meet coherent mixing conditions. As such, the maximum distance to the target 290 may be limited to less than 30 millimeters. However, according to some example embodiments, the use of a telecentric lens 300 with a 25 millimeter diameter may increase the maximum distance to the target 290 to be about 140 millimeters, resulting in an increase of about 110 millimeters.

As implemented in a variety of applications, the object beam 254 of the holographic imaging system 202, while interacting with the target 290, may also be subjected to undesired scatter in the form of volumetric scatter caused, for example, by the presence of non-target scattering material such as tissue, water, the atmosphere, or the like, within the volume surrounding the target 290. This scattering introduces noise into the scattered object beam 256 in the form of diffuse light (diffuse photons) that is not useful for generating a holographic image of the target 290, but can dominate the photons making up the scattered object beam 256. For example, in some instances, more than 95% of the photons of the raw scattered object beam 256 may be noise in the form of diffuse light. As such, an ability to capture and accurately record phase information and maximize contrast in the scattered object beam 256 may be limited by the presence of diffuse light. Therefore, it would be beneficial to remove or filter at least some of this diffuse light to improve the signal-to-noise ratio of the scattered object beam 256 prior to being mixed with the reference beam 252 and being received by the imaging array 220. While mixing performed by the combiner 240 may operate to mitigate the impact of some diffuse light, the inclusion of the pre-filter 302 comprising the telecentric lens 300 and the spatial filter 310 in the optical hardware 212 may operate to also perform pre-filtering of the noise in the form of diffuse light in the scattered object beam 256. Additionally, the pre-filter 302 may enhance the signal-to-noise ratio by increasing the numerical aperture of the holographic imaging system 202 relative to a numerical aperture that may be offered by the imaging array 220 alone. In the context of the previous description regarding increasing the maximum distance to the target 256, if the target 290 is located 140 millimeters away from the imaging array 220 without the pre-filter 302 (including the telecentric lens 300), the imaging array 220 may only be able to collect about 1 degree of scattered light, thereby greatly limiting the effective numerical aperture of a system.

According to some example embodiments, the telecentric lens 300 may be comprised of a collection of lenses and a spatial Fourier filter that operate together to perform the functions of the telecentric lens 300 described herein, such as, for example, a magnification operation and a filtering operation. The telecentric lens 300, according to some example embodiments, may provide an orthographic projection of the scattered object beam 256, which may magnify the scattered object beam 256 by a fixed amount, regardless of the distance between the optical hardware 212 and the target 290. The telecentric lens 300 may have a focal length range, within which proper focusing of the scattered object beam 256 may be performed without introducing blurring. According to some example embodiments, the telecentric lens 300 may operate with the spatial filter 310 (e.g., where the telecentric lens 300 and the spatial filter 310 are integrated into a common optical device). The telecentric lens 300 may also perform some degree of filtering due to the inclusion of the spatial Fourier filter 327 to perform filtering of diffuse light of the scattered object beam 256 in the Fourier domain. According to some example embodiments, each of the spatial Fourier filter 327 and the spatial filter 310 may be formed as an optical barrier with an aperture (e.g., pin-hole aperture) that is sized for the function of the filter.

As such, the telecentric lens 300 and the spatial filter 310 may operate together to focus the scattered object beam 256 and perform a filtering operation. In this regard, the spatial filter 310 may perform a filtering operation to remove noise or filter diffuse light from the scattered object beam 256, as the scattered object beam 256 passes through the telecentric lens 300. The telecentric lens 300 may comprise, for example, a first lens (e.g., lens 326 described further below) and a second lens (e.g., lens 328 described further below). For example, in some example embodiments, the telecentric lens 300 may be provided in a $4f$ configuration, where the target 290 is located in front of the first lens by one focal length of the first lens and the two lenses are separated by the sum of their two respective focal lengths. Additionally, in the $4f$ configuration, an image may be formed one focal length of the second lens behind the second lens in the telecentric lens 300, at a location that defines an image plane and the location of the spatial filter 310. The spatial filter 310 may be implemented as an optical device that is configured to alter the structure of a received light beam passing through the telecentric lens 300 by introducing, for example, a spatial optical aperture, located a focal length of the second lens behind the second lens when the telecentric lens 300 is in the $4f$ configuration. According to some example embodiments, the spatial filter 310 may remove noise from the received light beam by removing or blocking diffuse light from the scattered object beam 256 passing through the telecentric lens 300, and output, for example, only a transverse mode. According to some example embodiments, an aperture of the spatial filter 310 may also be sized to match the dimensions of the desired target 290. Sizing the aperture of the spatial filter 310 to match the dimensions of the target may facilitate an ability magnify the scattered object beam 256 from the volumetric scatterers adjacent the target 290, such as tissue, thereby making the scattered object beam 256 appear to be much larger than the scattered object beam 256 actually is. Such an increase in optical scatter diameter may impact contrast in the reconstructed image.

Note that while example embodiments are shown in the $4f$ configuration, it is contemplated that some example embodiments may be implemented in other configurations. For example, according to some example embodiments, a $2f$ configuration may also be implemented. In a $2f$ configuration, the telecentric lens 300 may comprise one lens, and the single lens may be located two focal lengths of the lens away from the target 290. However, regardless of whether the $4f$ or $2f$ configuration is implemented, the spatial Fourier filter 327 may be placed at the Fourier plane and the spatial filter 310 may be placed at the image plane.

According to some example embodiments, a holographic imaging system (e.g. holographic imaging system 200 or 202) may have a maximum coherent mixing angle θ between the scattered object beam 256 and the reference beam 252 that may be incident upon the imaging array 220. The maximum coherent mixing angle θ may be a function of the wavelength X of the light incident upon the imaging array 220 and the width of the optical sensors, also referred to as the pixel width Δε, of the imaging array 220. Light that is incident upon the imaging array 220 that is at an angle larger than the maximum coherent mixing angle θ, according to some example embodiments, may not be useful for coherent detection because, for example, optical phase information may only be included in non-diffuse light (e.g., ballistic and quasi-ballistic light). According to some example embodiments, the relationship describing the maximum coherent mixing angle may be θ<λ/Δε. As an example, a maximum coherent mixing angle θ, for an imaging array 220, may be about five degrees, and thus light with an incident angle at less than five degrees, in this example, may be useful for coherent detection. Based on this maximum coherent mixing angle θ of the holographic imaging system 202, the aperture of the telecentric lens 300 and the spatial filter 310 may be selected or tuned to match the imaging array 220 in order to filter light with angles larger than the maximum coherent mixing angle θ from reaching the imaging array 220.

Figure 6:
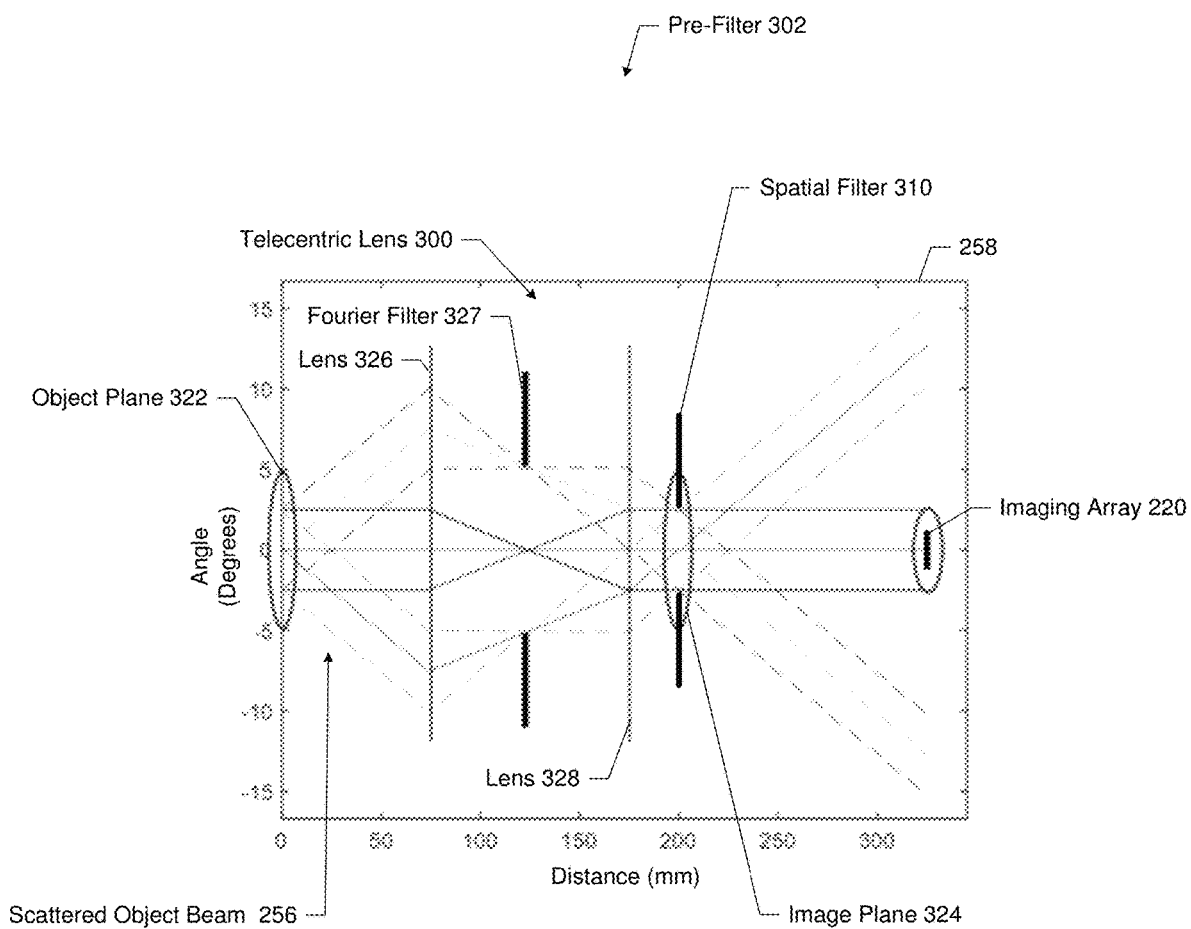
FIG. 6 illustrates a chart describing the operation of a telecentric lens according to some example embodiments.

To visualize the effect of pre-filter 302 comprising the telecentric lens 300 and the spatial filter 310, FIG. 6 shows a chart of the operation of the filtering operation according to an embodiment with respect to distance and angle of the light (e.g., the scattered object beam 256). In this regard, FIG. 6 illustrates an example embodiment of a pre-filter 302 comprising a telecentric lens 300 and a spatial filter 310. The telecentric lens 300 comprises a first lens 326, a second lens 328, and a spatial Fourier filter 327. The spatial filter 310 may be disposed on the imaging array-side of the second lens 328 at the image plane 324. In the configuration as shown in FIG. 6, the object plane 322 (i.e., the surface of the target 290 (not shown)) is located at 0 millimeters (mm), the first lens 326 of the telecentric lens 300 is located at the 75 mm, the spatial Fourier filter 327 is located at 125 mm, the second lens 328 of the telecentric lens 300 is located at 175 mm, the spatial filter 310 is located at the image plane 324 at 200 mm, and the imaging array 220 is located at 325 mm. The first lens 326 and the second lens 328 may have respective focal lengths of 50 mm. As shown in FIG. 6, the spatial Fourier filter 327 may comprise an aperture (or iris) of a defined angular width, such as from negative five degrees to positive five degrees. The spatial filter 310 may operate as an image plane filter and may have an aperture size that is matched to the size of the target 290 (not shown).

The scattered object beam 256 may be the reflection of the object beam 254 (not shown) from the target at the object plane 322. In this example, the scattered object beam 256 may include portions that scatter to positive and negative ten degrees that may be affected by the first lens 326 to be focused into the aperture of the spatial Fourier filter 327. Light at angles beyond positive and negative five degrees angular length of the spatial Fourier filter 327, having been affected by the first lens 326, are therefore blocked or filtered. The light that passes through the aperture of the spatial Fourier filter 327 is then impacted by the second lens 328 to cause the resultant light to be focused at the image plane 324 and be filtered by the spatial filter 310 for provision to the imaging array 220 (after being combined with the reference beam 252, which is not shown). Light that passes through the aperture of the spatial filter 310 near the limits (e.g., close to positive or negative five degrees) may be scattered by the second lens 328 away from the imaging array 220, and is therefore effectively filtered.

FIG. 7 illustrates an optical schematic representation of another example embodiment of a holographic imaging system 203 that is functionally similar to the holographic imaging system 202, but configured slightly differently. With respect to the distinctions, the scattered object beam 256 reflects back upon the object beam 254 and passes through the splitter 235 for mixing with the reference beam 252 at the combiner 240. The reference beam 252 is directed to the combiner 240 via the mirrors 251 and 253. The telecentric lens 300 and the spatial filter 310 may be components of the pre-filter 302. In this regard, the telecentric lens 300 may comprise the first lens 326, a spatial Fourier filter 327, and a second lens 328. According to some example embodiments, the first lens 326 may be located one focal length of the first lens 326 away from the target 290. The spatial Fourier filter 327 may be located one focal length of the first lens 326 away from the first lens 326 towards the imaging array 220 at the Fourier filter plane of the target 290. The second lens 328 may be located two focal lengths of the first lens 326 away from the first lens 326 towards the imaging array 220. The spatial filter 310 may be located one focal length of the second lens 328 away from the second lens 328 at the image plane. Further, the spatial filter 310 may be positioned to receive the scattered object beam 256 as provided by the telecentric lens 300, act upon the scattered object beam 256 as received, and provide a further filtered scattered object beam 257 to the combiner 240 for mixing and provision to the imaging array 220 as the interference beam 258. As mentioned above, the width or diameter of the aperture of the spatial filter 310 may be matched to the size of the target 290, which in some example embodiments may also be the diameter of the object beam 254, thereby blocking out at least some scattering caused by volumetric scatterers disposed between the target 290 and the system 200.

Example Frame Rate Optimization

Figure 2:
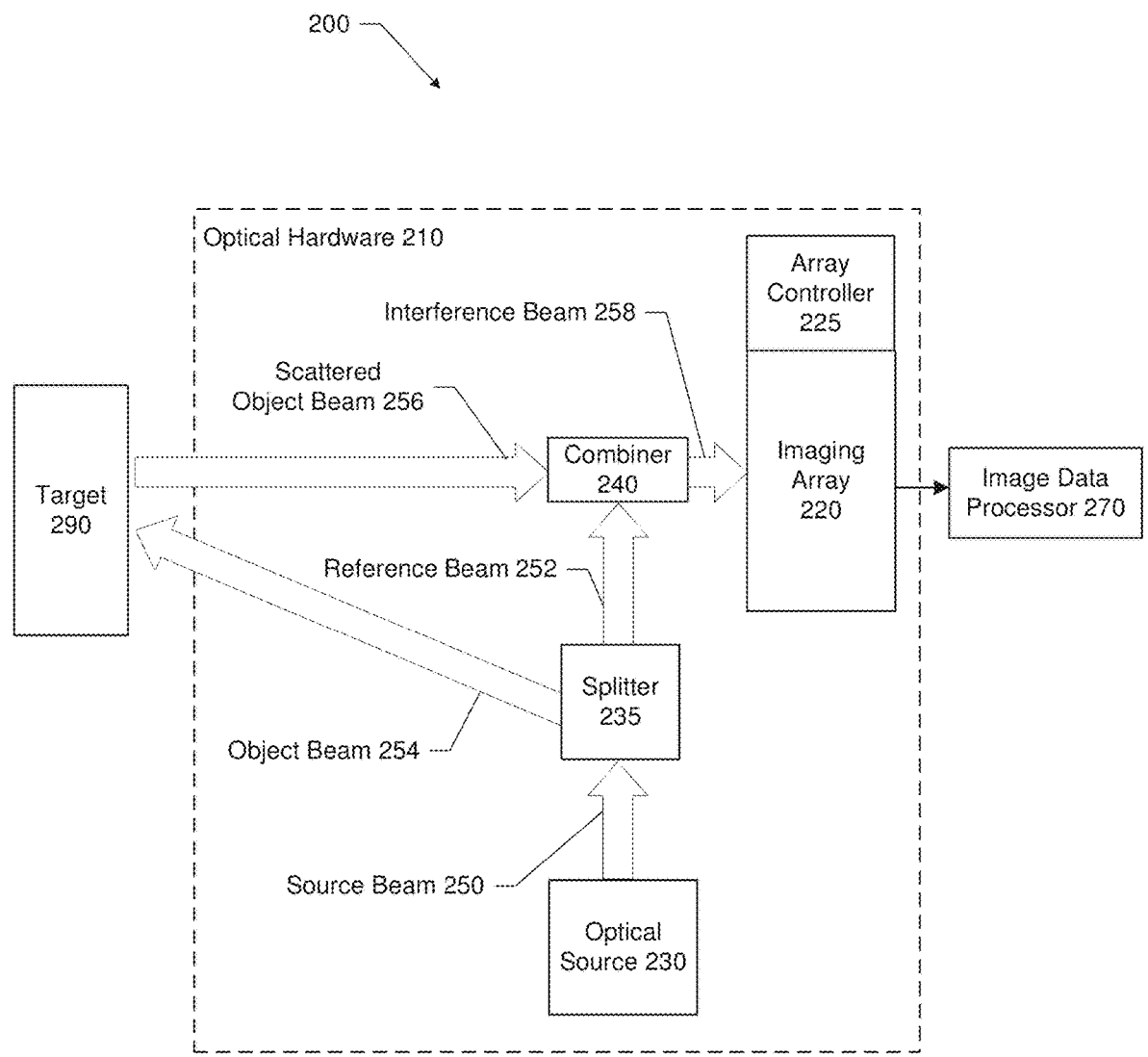
FIG. 2 illustrates a block diagram of a holographic imaging system in a reflective configuration according to some example embodiments.

Referring again to the holographic imaging system 200 of FIG. 2, an additional, or alternative, hardware-related optimization may be associated with the frame rate of the imaging array 220 as controlled by the array controller 225. In this regard, as mentioned above, the array controller 225 may operate to control a variety of configurable parameters of the imaging array 220, including, for example, the frame rate of the imaging array 220. The frame rate may be a capture speed of the imaging array 220 for successive capture events with respect to time, and the frame rate may be measured in frames per second. A frame may be a collection of light measurements made by imaging array 220 at each optical sensor of the imaging array 220. In this regard, according to some example embodiments, the array controller 225 may be configured to control the imaging array 220 to perform a series of frame capture events at a controlled frame rate. For each frame capture event, the imaging array 220 may be configured to make measurements of the interference beam 258 (e.g., at each optical sensor of the imaging array 220) to generate a frame of raw holographic data at a time of the frame capture event. Accordingly, the measurements taken at each optical sensor of the imaging array 220 may be aggregated based on, for example, a common time stamp to form a frame of raw holographic data. As such, frames of data may be captured in a time series at a given frame rate.

Since the frame rate may be a configurable parameter, according to some example embodiments, an optimized frame rate may be used for a particular application of the holographic imaging system 200. For example, with respect to capturing the motion of living tissue, a particular frame rate may be selected based on, for example, the expected motion of the tissue that is being targeted. In this regard, to image the motion of a target such as living tissue, accurate phase measurements of the interference beam 258 may be performed, according to some example embodiments, at frame rates having a frame capture period (i.e., time between frame captures) that is shorter than a decorrelation time of the target (e.g., tissue).

Decorrelation time may be based on the Brownian motion of the target's constituents (e.g., the tissue constituents). In other words, particles (e.g., cells, molecules, etc.) may move or vibrate at, for example, a frequency such that the movement of the particles after a certain duration of time leads to repositioning of the particles in a manner that has no meaningful relationship (i.e., no correlation) from the beginning of the duration to the end of the duration. This duration of time is the decorrelation time of the target comprising the particles. According to some example embodiments, the decorrelation time may be the time at which two successive image frames have a relative correlation score that is below $1/e=0.3678$. A calculation of the decorrelation time may be based on an autocorrelation function. Note that decorrelation time need not, and according to some example embodiments, is not calculated over an entire image. Rather portions of an image may be analyzed with respect to decorrelation, such as in a grid format or based on feature segments of image data.

Different targets, such as dermal targets (e.g., about 3-5 milliseconds), neural targets (e.g., about 0.5 milliseconds), etc., may generally have different decorrelation times and therefore frame rates for capturing motion of the target may be determined based on the decorrelation time for the given target. In this regard, if frame rates are used that are slower than the decorrelation time of the target, then the Brownian motion of the tissue may cause the tissue to be decorrelated such that scattering markers within the image are misconstrued or lost. However, by operating at frame rates with a capture period shorter than the decorrelation time of the target, the effect of decorrelation can be minimized during image acquisition and scattering markers may be tracked, allowing for the effect of decorrelation to be accounted for when imaging the motion of the tissue that is being targeted for analysis.

Figure 8:
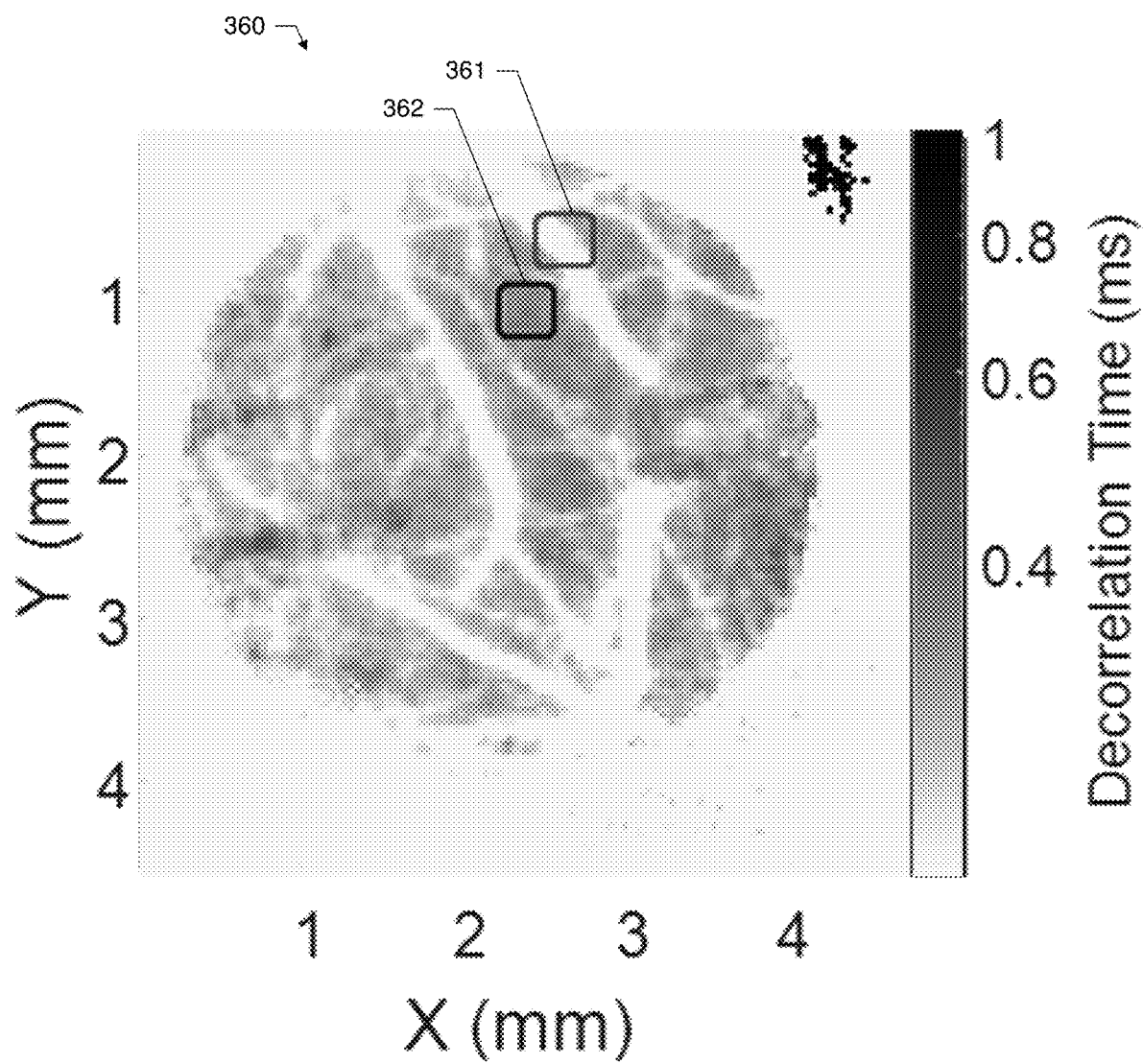
FIG. 8 illustrates a decorrelation time map according to some example embodiments.

Further with respect to decorrelation time, FIG. 8 illustrates a rendering of an example decorrelation time map 360 of an example target that includes both vascular and neural tissue, which may be generated by the holographic imaging systems described herein. In this regard, types of tissue can be identified based on the decorrelation time, which may be measured by a holographic imaging system. In this regard, because the vascular tissue is subjected to blood flow, the decorrelation time is relatively short and is indicated by being brighter in the image of FIG. 8. The dark regions have relatively slower decorrelation times and are associated with neural tissue. Accordingly, box 361 has been drawn over a vascular tissue region and box 362 has been drawn over a neural tissue region.

Figure 9:
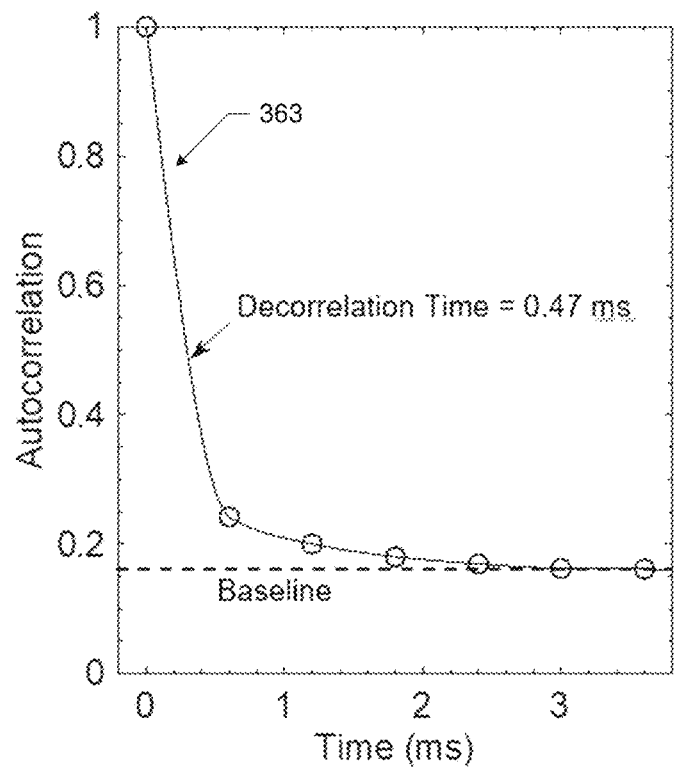
FIG. 9 illustrates an autocorrelation decay graph for vascular tissue according to some example embodiments.

FIG. 9 illustrates an example graph 363 of image autocorrelation with respect to time that occurs at the box 361 drawn over the vascular tissue as shown in the decorrelation map 360 of FIG. 8. As can be seen in the graph 363, with respect to the vascular tissue, correlation falls to less than 25% correlation in less than one millisecond. According to some example embodiments, sufficient correlation to determine, for example, motion within images may require a minimum correlation of 35% to perform a reliable analysis. As such, if frames of raw holographic data are captured at, for example, once every millisecond, then correlation has reduced between the frames to a degree that motion analysis may not be available to analyze due to the degree of decorrelation between the frames. Therefore, the frame rate may be set based on the expected decorrelation time. For example, using a 50% correlation base (rather than 35% as mentioned above), the decorrelation time shown in the graph 363 as provided in FIG. 9 may be 0.47 ms and the frame rate may be set accordingly. Increasing the correlation between two frames (in this example up to 50%) may decrease phase noise in the measurement and thus improve differential phase or displacement accuracy when generating an image.

Figure 10:
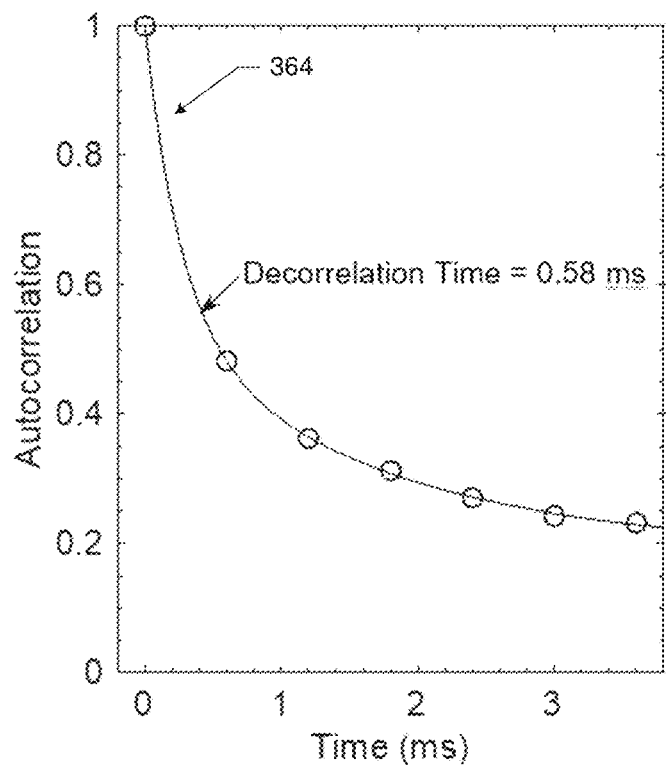
FIG. 10 illustrates an autocorrelation decay graph for neural tissue according to some example embodiments.

FIG. 10 illustrates an example graph 364 of image autocorrelation, similar to FIG. 9, however with respect to time that occurs at the box 362 drawn over the neural tissue as shown in the decorrelation map 360 of FIG. 8. As can be seen in the graph 364, with respect to the neural tissue, correlation is still above 35% at one millisecond. As such, if frames of raw holographic data are captured at, for example, once every millisecond, then sufficient correlation is present between the frames to perform a motion analysis of the tissue. Additionally, using a 50% correlation base (rather than 35% as mentioned above), the decorrelation time of the graph 364 as provided in FIG. 10 may be 0.58 ms and the frame rate can be set accordingly.

Rather than setting frame rates of the imaging array 220 based on the motion of interest (e.g., blood flow or vascular movement due to heart rate), the array controller 225 may be configured to control the imaging array 220 to operate at frame rate based on the decorrelation time of the target 290 (e.g., the tissue that is supporting the blood flow or vascular movement). As such, according to some example embodiments, the array controller 225 may be configured to operate above a lower limit or threshold frame rate based on the decorrelation time of the target 290. Accordingly, based on the application and the target 290, the array controller 225 may be configured to control the frame rate to be, for example, in the kilohertz range based on the decorrelation time. For example, ranges for the frame rates that the array controller 225 may cause the imaging array 220 to operate at may include 1 kHz to 1.2 kHz, 1.2 kHz to 5 kHz, 5 kHz to 10 kHz. According to some example embodiments, the array controller 225 may cause the imaging array 220 to operate at about (i.e., given component tolerances) 1.2 kHz, 5 kHz, 9.7 kHz, or 10 kHz. According to some example embodiments, the array controller 225 may cause the imaging array 220 to operate at greater than 1000 Hz.

Example Effective Frame Rate Optimization

As described above, relatively high speed frame rates may lead to an improvement in the holographic imaging, particularly over time, in order to capture information regarding motion of a target. To increase the frame rate, the array controller 225 may control the imaging array 220 to capture frames in accordance with the desired rate. However, imaging arrays that are able to operate at such high frame rates (e.g., faster than 1 kHz frame rates) may be costly. As such, an ability to "effectively" increase the frame rate of a holographic imaging system, without requiring an imaging array that actually operates at the desired frame rate would be useful, particularly if the same or relatively minor changes to the optical hardware could be implemented to realize such an effective increase in the frame rate.

According to some example embodiments, a holographic imaging system may be constructed that utilizes an off-axis configuration via two (or more) reference beams at different incident angles provided as pulses during a single frame capture event and integration time of the imaging array to create an effective increase in frame rate by including, for example, two effective frames of data in a single frame or single data capture. Sequential interference beams may be generated with different incident angles on the imaging array formed by the two references beams being mixed with respective scattered object beams. In this regard, the different incident angles may be introduced, for example, via mirrors or other optics that affect the path of the reference beams being tilted at different angles such that the first reference beam is incident upon the combiner 240 at a different angle than the second reference beam. Further, one of the reference beams may be time delayed relative to the other with the second interference beam being referred to as the time-delayed interference beam. This relative time delay may occur within the duration of a single integration time of the imaging array, as described above. While the wavelengths of the interference beams may be the same, the time delay and a variation in the incident angle may operate to "move" the data associated with the second interference beam away from the data associated with the first interference beam to avoid overlapping data. This approach, according to some example embodiments, may increase the effective frame rate of a holographic imaging system without requiring the imaging array to actually operate at an actual higher frame rate. Further, the holographic imaging system that may be realized in this manner may support a relatively high effective frame rate, while utilizing a less expansive imaging array operating a lower capture and data rates, but may have higher resolution.

Figure 11:
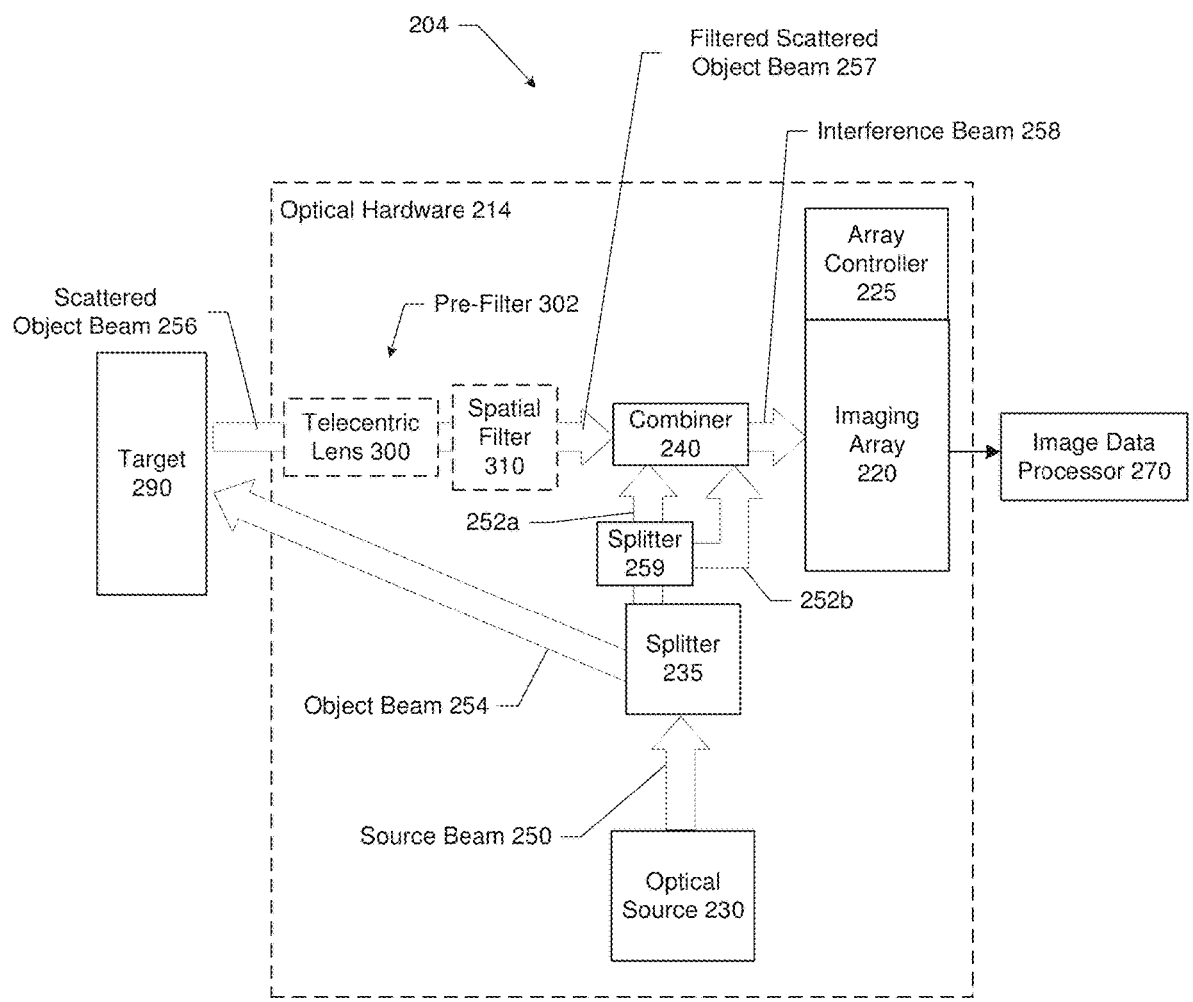
FIG. 11 illustrates a block diagram of a holographic imaging system for increasing an effective frame rate according to some example embodiments.

With reference now to FIG. 11, a block diagram of a holographic imaging system 204 according to an embodiment is shown that, again, builds upon of the holographic imaging system 200, and includes a variation of optical hardware 210 in the form of optical hardware 214 to realize the effective frame rate increase described above. Optical hardware 214, according to some example embodiments, may include additional hardware components such as, for example, a reference beam splitter 259 that functions to generate a first reference beam 252a and second reference beam 252b that are, for example, relatively time delayed and used to generate separate sets of holographic raw data within a single frame. The second reference beam 252b may also be referred to as a time-delayed reference beam. According to some example embodiments, the optical hardware 214 may, or may not, also include pre-filtering of the scattered object beam 256 via the pre-filter 302, for example, before being mixed with the reference beams 252a and 252b.

In this regard, the optical hardware 210 may be configured in a variety of ways to generate a sequence of optical pulses, such as a repeating sequence of two pulses according to some example embodiments, that can be used to generate the two reference beams 252a and 252b. Initially, rather than providing a constant output, the optical source 230 may provide a source beam 250 as a pulsed output. The optical source 230 may provide a pulsed output as the source beam 250 (or source beams 250), and the optical hardware 214 may be configured to convert a single pulse into a first reference beam 252a and a second reference beam 252b that is time delayed. To generate the first and second reference beams 252a and 252b, the first reference beam 252a may propagate through the path of the reference beam 252 as described above, while the second reference beam 252b may be split from the source beam 250 by a reference beam splitter 259 and routed through a longer path than the first reference beam 252a to introduce a time delay between the reference beams. A time delay may be introduced either through differences in the optical path length between the two different reference beams, or by placing an optical shutter in each of the two reference beam paths and then opening the optical shutters at slightly different times. In this regard, according to some example embodiments, the array controller 225 may be configured to control such optical shutters to expose the imaging array 220 to one of the two reference beams at a first time and the other of the two reference beams at a second, non-overlapping time.

Figure 12:
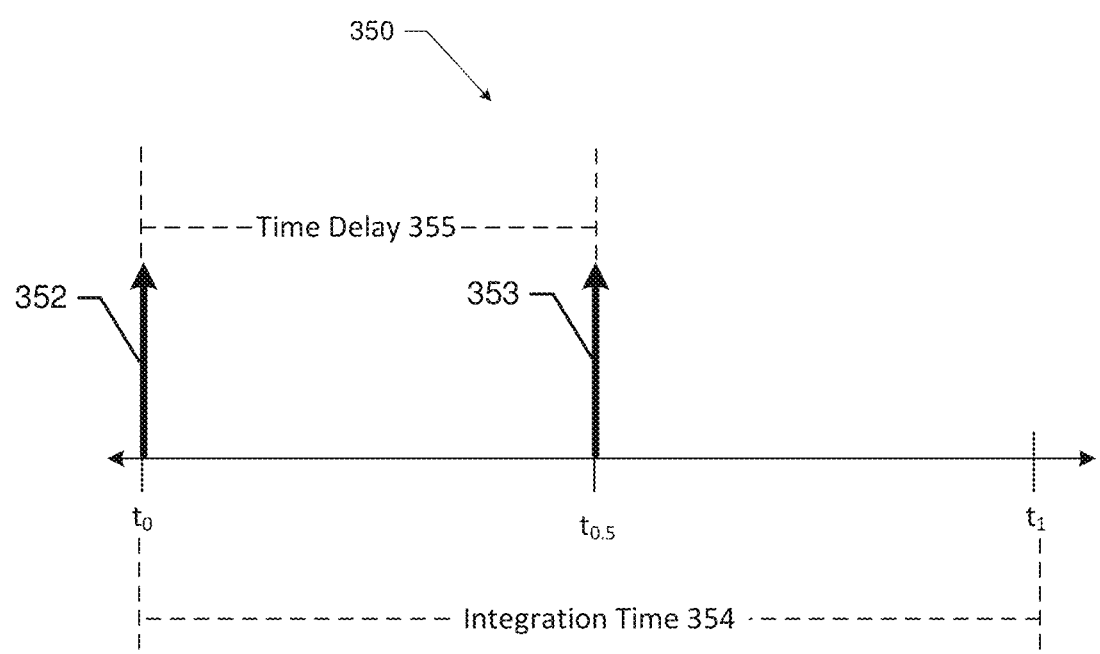
FIG. 12 illustrates a timing diagram for performing two capture events during a single integration time of an imaging array according to some example embodiments.

Regardless of how the reference beams 252a and 252b are formed and how the time delay is implemented, according to some example embodiments, due to the time delay between the reference beams 252a and 252b and an introduction of a variation in the incident angles of these two reference beams with regards to the object beam, a single frame capture event may be used to collect two "effective" frames of the data. As mentioned above, the difference in the incident angles between reference beam 252a and 252b may be introduced, for example, by a slight variation in the tilt of mirrors disposed within the respective optical paths of the reference beam 252a and the reference beam 252b, thereby causing the reference beam 252a to be incident upon the combiner 240 at a different angle (e.g., 1 degree difference or between about 1 to 3 degrees different) than the reference beam 252b. In this regard, as further described below with respect to FIG. 14, the mirror 260 in the optical path of reference beam 252b may have a slight tilt variation relative to the mirror 253 in the optical path of reference beam 252a. According to some example embodiments, the difference in the angles of the reference beam 252a and 252b may be limited to a maximum difference based on the optical wavelength of the optical source 230 and the size of the pixels/sensors of the imaging array 220. Further, the timing of the reference beams 252a and 252b may be synchronized with the integration time of the imaging array 220. In this regard, FIG. 12 illustrates an example timing diagram 350 that shows a time-based relationship between the interference beams 258 associated with the reference beams 252a and 252b received at the imaging array 220 and the integration time of the imaging array 220. The timing diagram 350 shows a single integration time 354 (i.e., a single capture event duration) for the imaging array 220. The integration time 354 begins at time $t_0$ (e.g., 0 ms) and ends at $t_1$ (e.g., 10 ms). From the time $t_0$ to time $t_1$, the imaging array 220 may be configured to capture light for conversion into raw holographic data and the imaging array 220 may be in a capturing mode. According to some example embodiments, the imaging array 220 may receive the interference beam 258 based on the reference beam 252a, indicated as pulse 352, at time $t_0$. After a time delay 355, and within the duration of the integration time 354, the imaging array 220 may then receive the interference beam 258 based on the reference beam 252b, indicated as pulse 353, at time $t_{0.5}$ (e.g., 5 ms), which may, according to some example embodiments, be half way through the duration of the integration time 354. As such, the imaging array 220 may measure the interference beam 258 at two separate times during a single integration time 354 due to the pulsed approach, thereby doubling the effective frame rate of the imaging array 220, because two effective frames of data may be generated during a single integration time 354. Also, because the interference beam 258 based on the first reference beam 252a has a different incident angle from the interference beam 258 based on the second reference beam 252b, and the difference in this angle is known, the data associated with the first reference beam 252a may be separated during, for example, post-processing, from the data associated with the second reference beam 252b and thereby treated as separate effective frames of data.

Figure 13:
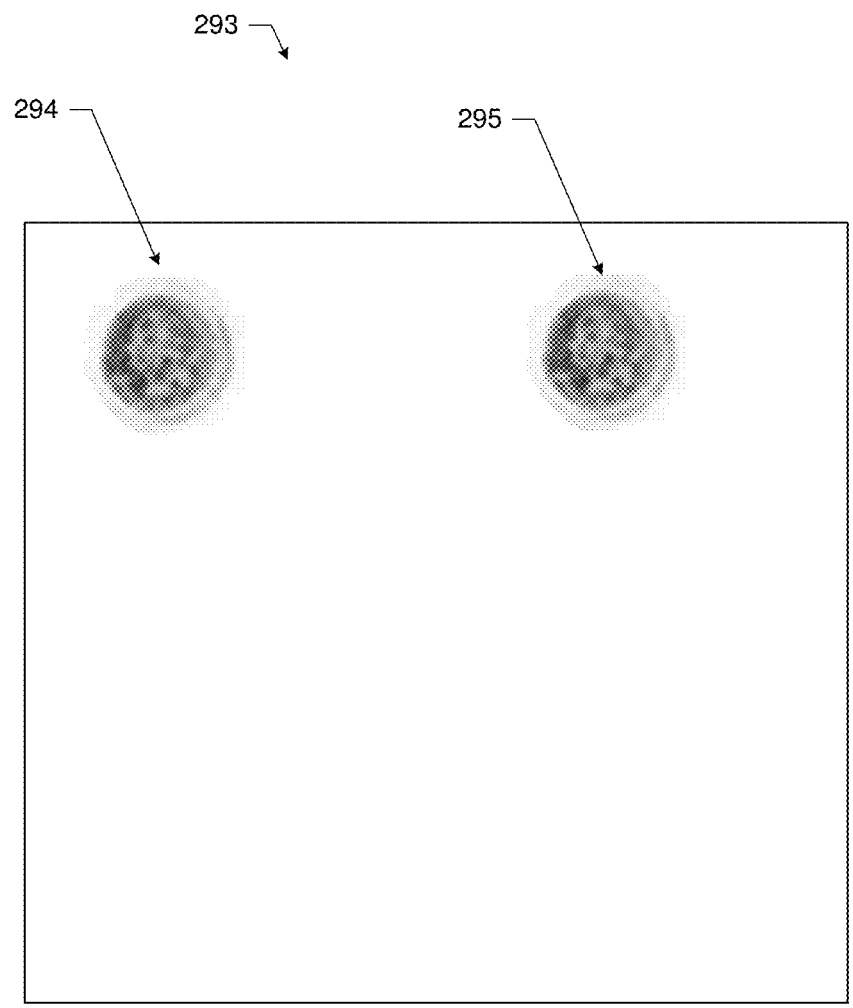
FIG. 13 illustrates a rendering of separate images based on a single frame of data according to some example embodiments.

Accordingly, the image data processor 270 may receive the raw holographic data for the frame and process the data to form an image. In this regard, the image data processor 270 may be configured to analyze the two holograms combined into the single frame of data and may render the two images, as illustrated in FIG. 13 according to an embodiment, with respect to a single frame 293 of the target 290. In this regard, the rendered image of the single frame of raw holographic data may include a first image 294 associated with reference beam 252a, and a second image 295 associated with reference beam 252b, after, for example, post-processing of the raw holographic data and image processing, as further described herein. Further, as an added efficiency that may be realized, if only the difference in the phase information between the two holograms is needed, the difference may be determined by subtracting the phase information of the image 294 from the phase information of the image 295 to identify the delta between the images. Such a subtraction may be performed, according to some example embodiments, on the raw holographic data prior to image processing.

Figure 14:
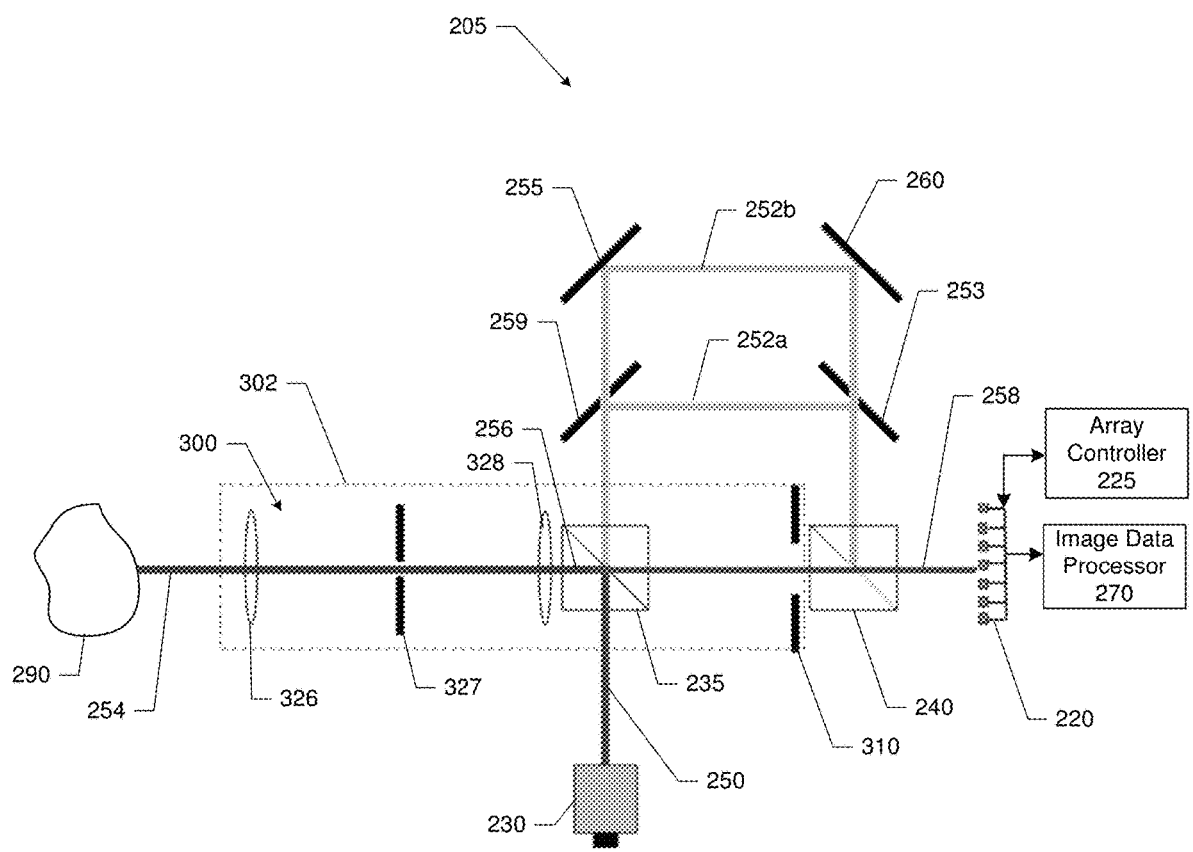
FIG. 14 illustrates an optical schematic of a holographic imaging system for increasing an effective frame rate according to some example embodiments.

FIG. 14 illustrates an optical schematic representation of another example embodiment of a holographic imaging system 205 that is functionally similar to the holographic imaging system 204, but configured slightly differently to support an effective frame rate increase as described above. With respect to the distinctions, the scattered object beam 256 reflects back upon the object beam 254 and passes through the splitter 235 for mixing with the reference beams 252a and 252b at the combiner 240 at different times. The optical source 230 may be configured to output the source beam 250 as a pulse sequence. The reference beam 252a may be directed to the combiner 240 via the reference beam splitter 259 and mirror 253, while the reference beam 252b, which may be split from the reference beam 252a by the reference beam splitter 259, may take a longer, time-delayed route and may be directed to the combiner 240 via the mirrors 255 and 260.

As such, according to some example embodiments, the holographic imaging system 205 may comprise a reference beam splitter 259 configured to split a time delayed reference beam 252b from the reference beam 252a. The imaging array 220 may be configured to receive the interference beam 258 associated with the reference beam 252a at a first time during a single integration time of the imaging array 220 and may be configured to receive a time delayed interference beam 258 associated with the time delayed reference beam 252b during the single integration time of the imaging array. An incident angle of the interference beam 258 on the imaging array 220 may be different from an incident angle of the time delayed interference beam 258 on the imaging array 220. The raw holographic data associated with the initial interference beam 258 may be differentiated from raw holographic data associated with the time delayed interference beam 258 based on the difference in the incident angle of the initial interference beam 258 on the imaging array 220 from an incident angle of the time delayed interference beam 258 on the imaging array 220.

Example Wavelength Optimization

According to various example embodiments, the selection of the wavelength for the holographic imaging system 200 may lead to improvements in imaging based on the type of target 290 being imaged. In this regard, the amount of scatter that particular target 290 creates in response to the object beam 254 may be a function of the wavelength of the object beam 254. As such, control and selection of, for example, the source beam 250 of the system 200, which may dictate the wavelength of the object beam 254, reference beam 252, and interference beam 258, may be a system parameter that can be optimized. As such, according to some example embodiments, the optical source 230 may be controlled, for example by the array controller 225, to output a source beam 250 at a wavelength that causes the target 290 to provide at least a threshold scatter level (e.g., a threshold intensity) in the scattered object beam 256.

For example, in neural applications that may involve penetration through the skull, the skull and the neural tissue may exhibit different scattering (i.e., different scatter coefficients) at certain wavelengths. Neural tissue may generate increasingly higher coefficients of scatter at shorter wavelengths (e.g., from 1100 nanometers to 600 nanometers) relative to the bone of the skull which may be relatively unaffected. As such, operation at shorter wavelengths may offer improved signal return (e.g., more scatter leading to increased signal strength) from the target neural tissue, while having relatively little effect on the (undesirable) scatter generated by the bone of the skull. Such an improvement in the signal return may be increasingly desirable in the context imaging at increasingly small volumes that may inherently suffer from low signal return.

According to some example embodiments, another source of optimization in the selection of the optical source 230 may be the choice of laser coherence length. Laser coherence length may define the distance over which light can travel and still constructively interfere with itself (i.e., maintain a threshold degree of coherence). According to some example embodiments, the coherence length of the source beam 250 of the optical source 230 may define the path-length difference between the object beam 254 and reference beam 252. Selecting a coherence length (or sensing volume) that matches or closely matches the volume or length over which the scattered object beam 256 exists from a target 290 may cause a reduction in an amount of background noise, while maximizing signal level. For example, when detecting neural activity, it may be advantageous to have the sensing volume (i.e., location of the target 290) to be limited to the top few millimeters of the cortex where the neural activity is stronger. Sensing at depths greater than that may increase the strength of background noise such as heart rate, since, for example, heart rate is present at all depths of the neural tissue.

Example Methods of Operation—Hardware

Figure 15:
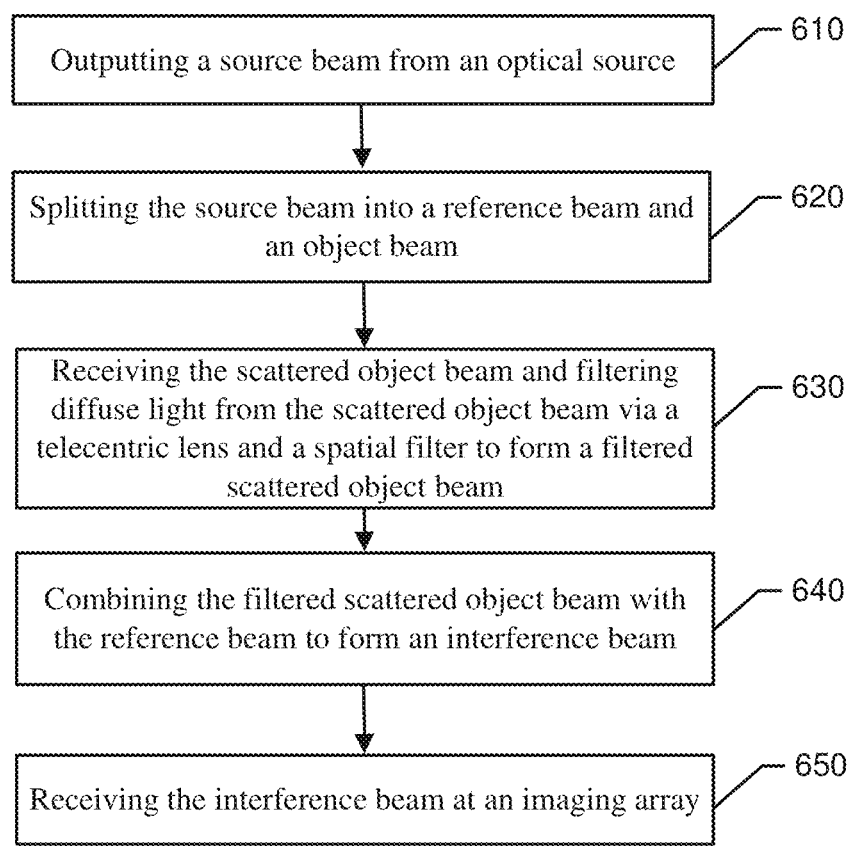
FIG. 15 illustrates a flow chart of an example method of operating a holographic imaging system according to some example embodiments.

According to some example embodiments, various methods for implementing a holographic imaging system are provided based on the techniques described herein. In this regard, FIG. 15 illustrates a flow chart of an example method according to some example embodiments. The example method may comprise, at 610, outputting a source beam from an optical source, and, at 620, splitting the source beam into a reference beam and an object beam. In this regard, the object beam may be incident on a target to form a scattered object beam. At 630, the example method may also comprise receiving the scattered object beam and filtering diffuse light from the scattered object beam via a telecentric lens and a spatial filter to form a filtered scattered object beam, and, at 640, combining the filtered scattered object beam with the reference beam to form an interference beam. Additionally, at 650, the example method may comprise receiving the interference beam at an imaging array.

Additionally, according to some example embodiments, the example method may further comprise magnifying the scattered object beam via the telecentric lens and applying the magnified scattered object beam to the spatial filter to perform filtering to form the filtered scattered object beam. Additionally or alternatively, the example method may further comprise filtering light from the scattered object beam, via the telecentric lens and the spatial filter, having an incident angle greater than a maximum coherent mixing angle for a holographic imaging system. Additionally or alternatively, the example method may comprise controlling the imaging array to perform a series of frame capture events at a controlled frame rate. In this regard, for each frame capture event, the example method may further comprise capturing measurements of the interference beam and converting the measurements into a frame of raw holographic data at a time of the frame capture event. A frame rate period based on the controlled frame rate, according to some example embodiments, may be shorter than a decorrelation time of the target. Additionally or alternatively, the controlled frame rate may be greater than 1000 Hertz. According to some example embodiments, the example method may additionally or alternatively comprise splitting a time delayed reference beam from the reference beam, and receiving, at the imaging array, the interference beam associated with the reference beam at a first time during a single integration time of the imaging array and receiving a time delayed interference beam associated with the time delayed reference beam during the single integration time of the imaging array. In this regard, according to some example embodiments, an incident angle of the interference beam on the imaging array may be different from an incident angle of the time delayed interference beam on the imaging array. Additionally or alternatively, raw holographic data associated with the interference beam may be differentiated from raw holographic data associated with the time delayed interference beam based on the difference in the incident angle of the interference beam on the imaging array from an incident angle of the time delayed interference beam on the imaging array. Additionally or alternatively, outputting the source beam may comprise outputting the source beam at a wavelength that causes the target to provide at least a threshold scatter level in the scattered object beam.

Example Holographic Imaging System—Processing

Figure 16:
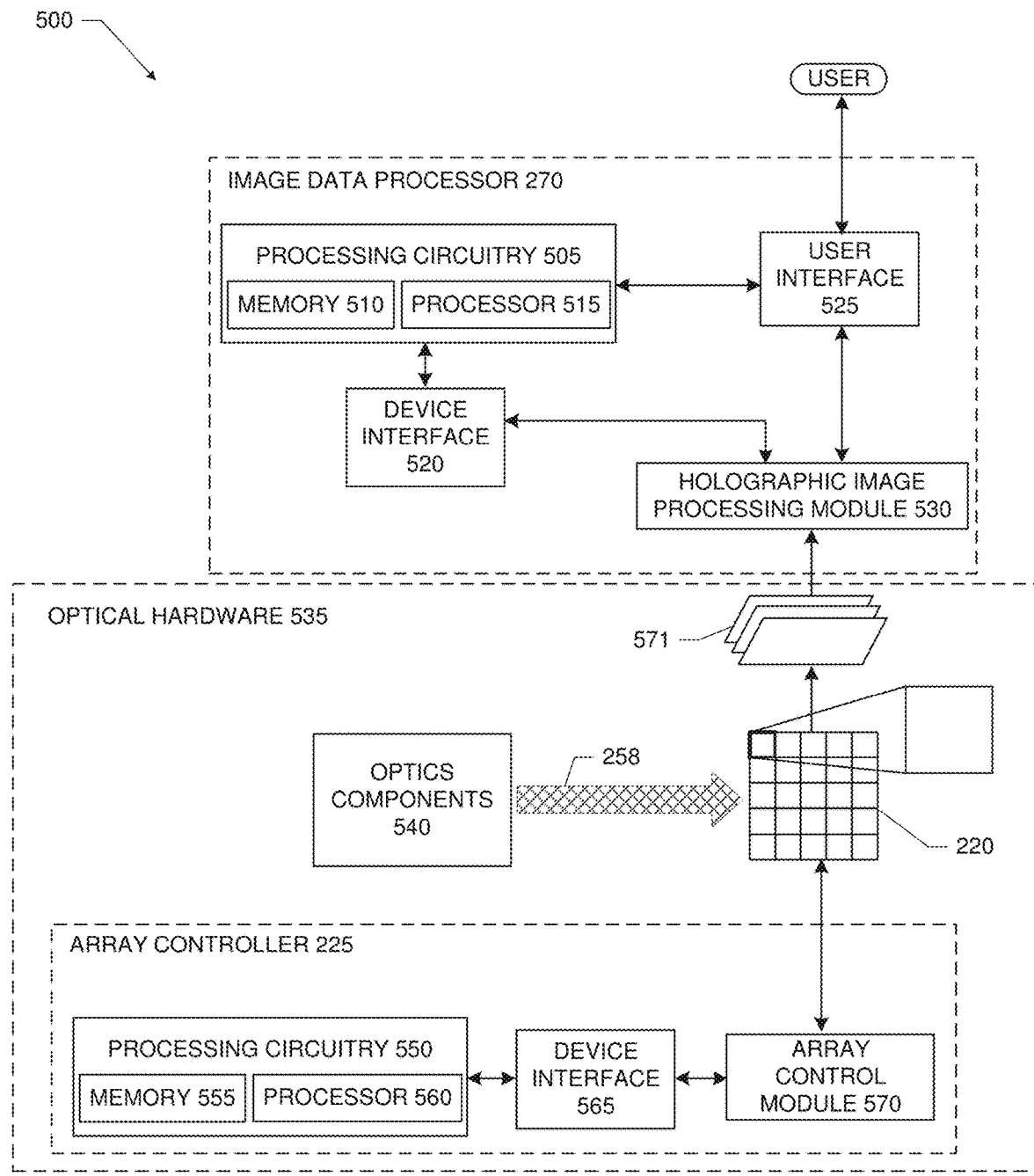
FIG. 16 illustrates a block diagram of a holographic imaging system including processing component details according to some example embodiments.

In view of the foregoing, FIG. 16 illustrates a block diagram of a holographic imaging system 500 according to an embodiment that highlights the processing components of the system. In this regard, the holographic imaging system 500 may be an embodiment of any of the holographic imaging systems described herein with optical hardware 535 being representative of any of the optical hardware configurations described herein. In this regard, optic components 540 may be any configuration of the components described herein to generate an interference beam 258 that is incident upon the imaging array 220. The following therefore provides additional detail with regard to the configuration of the array controller 225 and the image data processor 270 in combination with any configuration of the optical components 540.

The array controller 225 may include or otherwise be in communication with processing circuitry 550, which may be configurable to perform actions in accordance with example embodiments described herein. As such, for example, at least some of the functions attributable to the array controller 225 may be carried out by or otherwise instructed by the processing circuitry 550. The processing circuitry 550 may therefore provide the hardware for implementing, for example, software to configure the system for analysis techniques consistent with example embodiments. The control of the imaging array 220, as well as other hardware elements of the optics components 540 (e.g., optical source 230) may be performed by the array controller 225 via the processing circuitry 550.

The processing circuitry 550 may be configured to perform control function execution and/or other processing and management services according to some example embodiments with respect to the imaging array 220. In some embodiments, the processing circuitry 550 may be embodied as a chip or chip set. In other words, the processing circuitry 550 may comprise one or more physical packages (e.g., chips) including materials, components and/or wires on a structural assembly (e.g., a baseboard).

In an example embodiment, the processing circuitry 550 may include one or more instances of a processor 560 and memory 555 that may be in communication with or otherwise control a device interface 565 and, in some cases, a user interface (not shown). As such, the processing circuitry 550 may be embodied as one or more instances of a circuit chip (e.g., an integrated circuit chip) configured (e.g., with hardware, software or a combination of hardware and software) to perform operations described herein.

The device interface 565 may include one or more interface mechanisms for enabling communication with other external devices (e.g., output devices, input devices and/or the like) or internal functional components of the holographic imaging system 500, including, for example, the imaging array 220. In some cases, the device interface 565 may be any means such as a device or circuitry embodied in either hardware, or a combination of hardware and software that is configured to receive and/or transmit data from/to devices in communication with the processing circuitry 550.

According to some example embodiments, the memory 555 may include one or more non-transitory memory devices such as, for example, volatile and/or non-volatile memory that may be either fixed or removable. The memory 555 may be configured to store information, data, applications, instructions or the like for enabling the array controller 225 to carry out various functions in accordance with example embodiments. For example, the memory 555 could be configured to buffer input data for processing by the processor 560. Additionally or alternatively, the memory 555 could be configured to store instructions for execution by the processor 560. As yet another alternative or additional feature, the memory 555 may include one or more databases that may store a variety of data sets indicative of patterns or work flows that are configured to trigger specific responses or algorithms, control techniques, processing algorithms and/or the like to be employed for the execution of example embodiments. Among the contents of the memory 555, applications may be stored for execution by the processor 560 in order to carry out the functionality associated with each respective application. In some cases, the applications may include directions for control of the imaging array 220 via, for example, configurable parameters such as frame rate. In particular, in some cases, the applications may include instructions for directing operation of a array control module 570 which may be configured to control the array controller 225 via the processing circuitry 550 to perform various functionalities as described herein.

The processor 560 may be embodied in a number of different ways. For example, the processor 560 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 560 may be configured to execute instructions stored in the memory 555 or otherwise accessible to the processor 560. As such, whether configured by hardware or by a combination of hardware and software, the processor 560 may represent an entity (e.g., physically embodied in circuitry in the form of processing circuitry 550) capable of performing operations according to embodiments described herein while configured accordingly. Thus, for example, when the processor 560 is embodied as an ASIC, FPGA or the like, the processor 560 may be specifically configured hardware for conducting the operations described herein. As another example, when the processor 560 is embodied as an executor of software instructions, the instructions may specifically configure the processor 560 to perform the operations described herein.

In an example embodiment, the processor 560 (or the processing circuitry 550) may be embodied as, include, or otherwise control the array controller 225. As such, in some embodiments, the processor 560 (or the processing circuitry 550) may be said to cause each of the operations described in connection with the array controller 225 and/or the array control module 570 by directing the array controller 225 and/or the array control module 570 to undertake the corresponding functionalities responsive to execution of instructions or algorithms configuring the processor 560 (or processing circuitry 550) accordingly.

Array control module 570 may be configured to control the operation of the array controller 225 in accordance with the functionalities described herein. In this regard, for example, the array control module 570 may configure various parameters of the imaging array 220 based on, for example, the type of application that the holographic imaging system 500 is being utilized to perform. In this regard, for example, the array control module 570 may be configured to control the imaging array 220 to perform a series of frame capture events at a controlled frame rate. In this regard, according to some example embodiments, for each frame capture event, the measurements of the interference beam may be taken by the imaging array 220 under control of the array controller 225 via the array control module 570, and the measurements may be converted into a frame of raw holographic data at a time of the frame capture event. Further, the array control module 570 may be configured to control the imaging array 220 to have a frame rate period based on the controlled frame rate that is shorter than a decorrelation time of the target 290. In this regard, according to some example embodiments, the controlled frame rate may be greater than 1000 Hertz.

The image data processor 270 may include or otherwise be in communication with processing circuitry 505, which is configurable to perform actions in accordance with example embodiments described herein. As such, for example, at least some of the functions attributable to the image data processor 270 may be carried out by or otherwise instructed by the processing circuitry 505. The processing circuitry 505 may therefore provide the hardware for implementing, for example, software to configure the system for analysis techniques consistent with example embodiments for image processing. In this regard, the image data processor 270 may be configured to receive raw holographic data from the imaging array 220 and perform various types of processing on the data to, for example, generate an image of a target for analysis.

The image data processor 270 may include or otherwise be in communication with processing circuitry 505 that is configurable to perform actions in accordance with example embodiments described herein. As such, for example, at least some of the functions attributable to the image data processor 270 may be carried out by or otherwise instructed by the processing circuitry 505. The processing circuitry 505 may therefore provide the hardware for hosting software to configure the system for analysis techniques consistent with example embodiments.

The processing circuitry 505 may be configured to perform data processing, control function execution and/or other processing and management services some example embodiments. In some embodiments, the processing circuitry 505 may be embodied as a chip or chip set. In other words, the processing circuitry 505 may comprise one or more physical packages (e.g., chips) including materials, components and/or wires on a structural assembly (e.g., a baseboard).

In an example embodiment, the processing circuitry 505 may include one or more instances of a processor 515 and memory 510 that may be in communication with or otherwise control a device interface 520 and, in some cases, a user interface 525. As such, the processing circuitry 505 may be embodied as one or more instances of a circuit chip (e.g., an integrated circuit chip) configured (e.g., with hardware, software or a combination of hardware and software) to perform operations described herein.

The user interface 525 (if implemented) may be in communication with the processing circuitry 505 to receive an indication of an user input at the user interface 525 and/or to provide an audible, visual, mechanical, or other output to the user. As such, the user interface 525 may include, for example, a display, printer, one or more buttons or keys (e.g., function buttons), and/or other input/output mechanisms (e.g., keyboard, touch screen, mouse, microphone, speakers, cursor, joystick, lights and/or the like). The user interface 525 may display information, for example, that is associated with an image of a target as described herein. In this regard, raw holographic data may be processed to form images (e.g., a decorrelation map) and information associated therewith for presentation, for example, on a display of the user interface 525 based on instructions executed by the processing circuitry 505 for the analysis of the data according to methodologies and/or algorithms as provided herein. Moreover, in some cases, the user interface 525 may include options for selection of one or more reports or displays to be generated based on the analysis of a given data set.

The device interface 520 may include one or more interface mechanisms for enabling communication with other external devices (e.g., output devices, input devices and/or the like) or internal functional components of the holographic imaging system. In some cases, the device interface 520 may be any means such as a device or circuitry embodied in either hardware, or a combination of hardware and software that is configured to receive and/or transmit data from/to devices in communication with the processing circuitry 505.

In an exemplary embodiment, the memory 510 may include one or more non-transitory memory devices such as, for example, volatile and/or non-volatile memory that may be either fixed or removable. The memory 510 may be configured to store information, data, applications, instructions or the like for enabling the image data processor 270 to carry out various functions in accordance with example embodiments. For example, the memory 510 could be configured to buffer input data for processing by the processor 515. Additionally or alternatively, the memory 510 could be configured to store instructions for execution by the processor 515. As yet another alternative or additional feature, the memory 510 may include one or more databases that may store a variety of data sets indicative of patterns that are configured to trigger specific responses or algorithms, image data processing techniques, processing algorithms and/or the like to be employed for the execution of example embodiments. Among the contents of the memory 510, applications may be stored for execution by the processor 515 in order to carry out the functionality associated with each respective application. In some cases, the applications may include directions for control of the image data processor 270 to process images based on raw holographic data received from the imaging array 220. In particular, in some cases, the applications may include instructions for directing operation of a holographic image processing module 530 relative to sets or frames of raw holographic data 571. In some cases, the applications may further include directions for generating an output as one or more reports, imaging displays, or other outputs of data or analytical work product associated with analysis of the raw holographic data 571 as described herein.

The processor 515 may be embodied in a number of different ways. For example, the processor 515 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 515 may be configured to execute instructions stored in the memory 510 or otherwise accessible to the processor 515. As such, whether configured by hardware or by a combination of hardware and software, the processor 515 may represent an entity (e.g., physically embodied in circuitry in the form of processing circuitry 505) capable of performing operations according to example embodiments described herein while configured accordingly. Thus, for example, when the processor 515 is embodied as an ASIC, FPGA or the like, the processor 515 may be specifically configured hardware for conducting the operations described herein. Alternatively, as another example, when the processor 515 is embodied as an executor of software instructions, the instructions may specifically configure the processor 515 to perform the operations described herein.

In an example embodiment, the processor 515 (or the processing circuitry 505) may be embodied as, include or otherwise control the image data processor 270. As such, in some embodiments, the processor 515 (or the processing circuitry 505) may be said to cause each of the operations described in connection with the image data processor 270 and/or the holographic image processing module 530 by directing the image data processor 270 and/or the holographic image processing module 530 to undertake the corresponding functionalities responsive to execution of instructions or algorithms configuring the processor 515 (or processing circuitry 505) accordingly.

The holographic image processing module 530 may be generally configured to process one or more frames of raw holographic data 571 received from the imaging array 220 to generate an image (e.g., a complex image) based on the raw holographic data. According to some example embodiments, the processing of the raw holographic data or the frames of raw holographic data may be performed in a variety of ways to obtain a variety of results, including but not limited to, the generation of an image of the target 290. In this regard, according to some example embodiments, the holographic image processing module 530 may be configured to perform functionalities associated with computer-generated holography. As mentioned above, the image data processor 270 and, more specifically, the holographic image processing module 530 may be configured to receive the raw holographic data 571 from the imaging array 220 or the array controller 225. In this regard, the raw holographic data 571 may represent the measurements of the interference beam 258 received at the imaging array 220 (i.e., after the scattered object beam 256 and the reference beam 252 have been coherently mixed). The holographic image processing module 530 may be configured to generate a complex image from the raw holographic data 571 received from the imaging array 220 or the array controller 225 based on magnitude and phase information from the measurements. Creation of the complex image may be performed in a variety of ways. For example, according to some example embodiments, the holographic image processing module 530 may be configured to apply a transform to the raw holographic data 571, such as a Fourier transform, a Fresnel transform, or the like. In this regard, point-source approaches may be utilized, which may include ray tracing, in the generation of a complex image. Additionally, the holographic image processing module 530 may be configured to apply a convolution and angular spectrum processing to the raw holographic data 571. The result may be a complex image generated by the holographic image processing module 530. The complex image may comprise both magnitude and phase information about the target 290 that may be subjected to further processing as provided herein.

The following provides a description of a number of different configurations of the holographic image processing module 530 that may be used alone or in combination to further improve and optimize the operation of the holographic imaging system 500.

Figure 17:
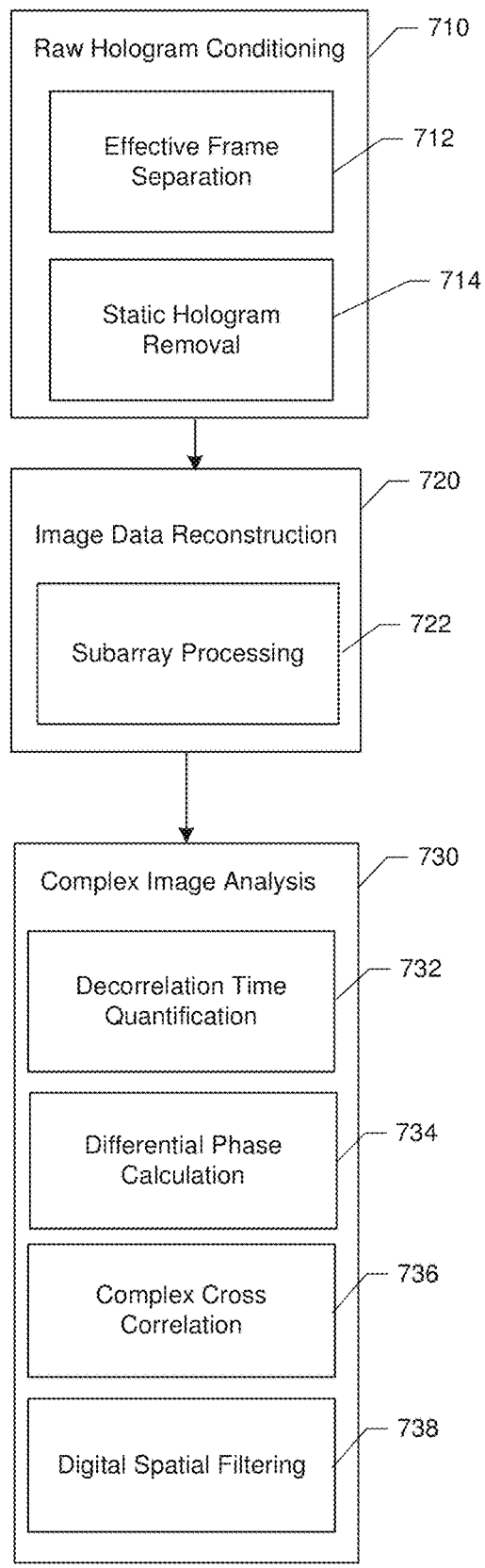
FIG. 17 illustrates a flow chart of raw holographic data image processing techniques according to some example embodiments.

FIG. 17 illustrates a high-level flow chart according to an embodiment identifying some of the techniques that may be implemented by the image data processor 270 and the holographic image processing module 530 to, for example, improve image quality and therefore the analysis of the images. In this regard, according to some example embodiments, raw hologram conditioning may be performed at 710, which may include effective frame separation at 712 and static hologram removal at 714. Further, image data reconstruction at 720 may be performed, which may include subarray processing at 722. Additionally, complex image analysis may be performed at 730, which may include decorrelation time quantification at 732, differential phase calculation at 734, complex cross correlation at 736, and digital spatial filtering at 738. The above techniques are described in more detail below.

Example Effective Frame Separation

With regard to effective frame separation 712, and following from the description of the holographic imaging system 204 and the implementation of an effective frame rate increase, the holographic image processing module 530 may be configured to receive a frame of raw holographic data that comprises two effective frames, and separate the raw holographic data for the first effective frame from the raw holographic data for the second effective frame. In this regard, as described above, a single frame of raw holographic data may be generated by, for example, two time-separated interference beam pulses during a single integration time of the imaging array 220. Each of the interference beams that are incident on the imaging array 220 during the single integration time are incident at different angles. According to some example embodiments, the different incident angles for the interference beams may be known to the holographic image processing module 530 and, as such, the holographic image processing module 530 may be configured to use the incident angle of the first interference beam to determine the portion of the frame data that is associated with the first interference beam for storage and analysis as a first effective frame of raw holographic data. Additionally, the holographic image processing module 530 may be configured to use the incident angle of the second interference beam to determine the portion of the frame data that is associated with the second interference beam for storage and analysis as a second effective frame of raw holographic data. After separating the raw holographic data of the first effective frame from the raw holographic data of the second effective frame, the respective data of these effective frames may be processed and analyzed in the same manner as described herein with respect to any frame of raw holographic data.

Example Static Hologram Removal

As described above, the image data processor 270 and the holographic image processing module 530 may receive the raw holographic data directly from the imaging array 220 for storage and further analysis, or the image data processor 270 may perform some preliminary processing of the raw holographic data, such as separation of effective frames as described above, and then store the raw holographic data for further analysis. Regardless of the operations involved in obtaining a series of frames of raw holographic data, according to some example embodiments, the holographic image processing module 530 may be configured to perform raw hologram conditioning 710 on the frames of raw holographic data via static hologram removal 714.

In this regard, depending on the application being performed by the holographic imaging system 500, there may be a need to remove data associated with slow moving or static particles or features within the raw holographic data. For example, in a neural tissue imaging application, it may be desirable to remove information introduced into the raw holographic data by the presence of the bone of the skull, since this information is not of interest in the application and therefore constitutes noise. According to some example embodiments, when the target 290 changes at a faster rate (i.e., at a high frequency) than other particles or features that are not of interest and only contribute to noise, the contribution of those particles or features can be removed (directly) from the raw holographic data based on the frequency of movement of those particles or features. In other words, based on the expected motion of the target 290, a movement frequency threshold may be determined and data that exhibits motion at or below the movement frequency threshold may be removed from the frames of raw holographic data. In this regard, according to some example embodiments, vascular-associated movement (e.g., movement at about 100 Hz from the heart beat) or respiratory-related movement (e.g., movement at about 5 Hz from breathing) may be other examples of relatively low frequency movements that may provide a basis for removal or filtering.

According to some example embodiments, the holographic image processing module 530 may be configured to apply a movement frequency threshold to a series of frames of raw holographic data and remove or subtract out data from the from the frames of raw holographic data that are associated with movement that is at or below the movement frequency threshold. In other words, according to some example embodiments, the holographic image processing module 530 may be configured to remove data components within frames of raw holographic data that are associated with the particle motion having a motion frequency that is less than a movement frequency threshold to form conditioned raw holographic data for further analysis. Further, the holographic image processing module 530 may be configured to average a number of frames of raw holographic data (i.e., over a time period) to form an average frame, and then subtract the data of the average frame from the raw holographic data of the one or more frames to generate the conditioned raw holographic data. The average frame may, according to some example embodiments, be generated based on a minimum number of frames of raw holographic data. In this way, data that is regularly present across a number of frames of raw holographic data is considered to be static and can be removed or filtered. Alternatively, according to some example embodiments, a high-pass filter may be employed to remove the low-frequency motion data.

Figure 18:
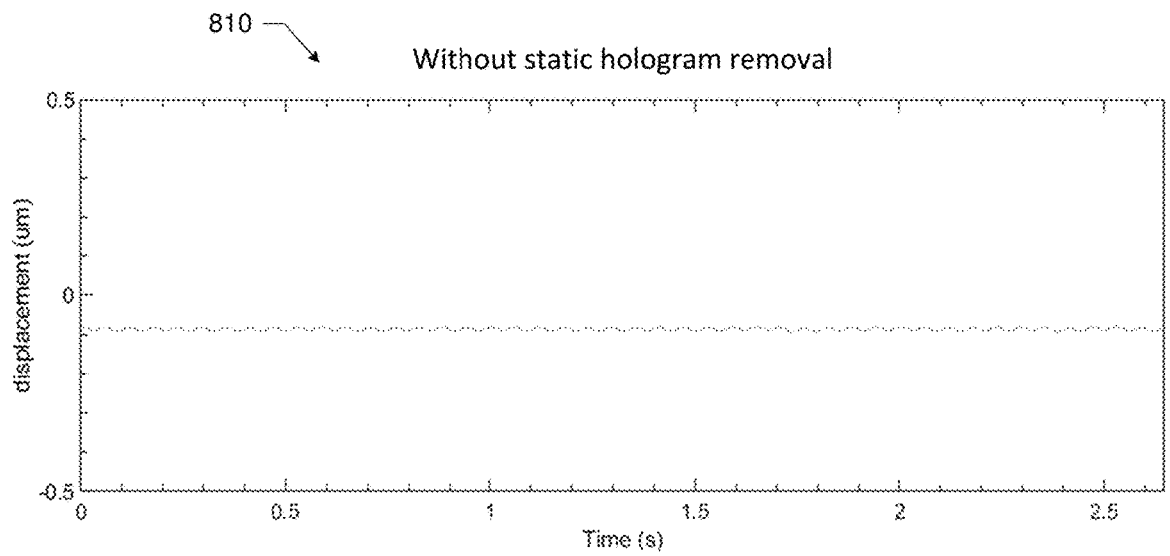
FIG. 18 illustrates an example signal response without performing static hologram removal according to some example embodiments.
Figure 19:
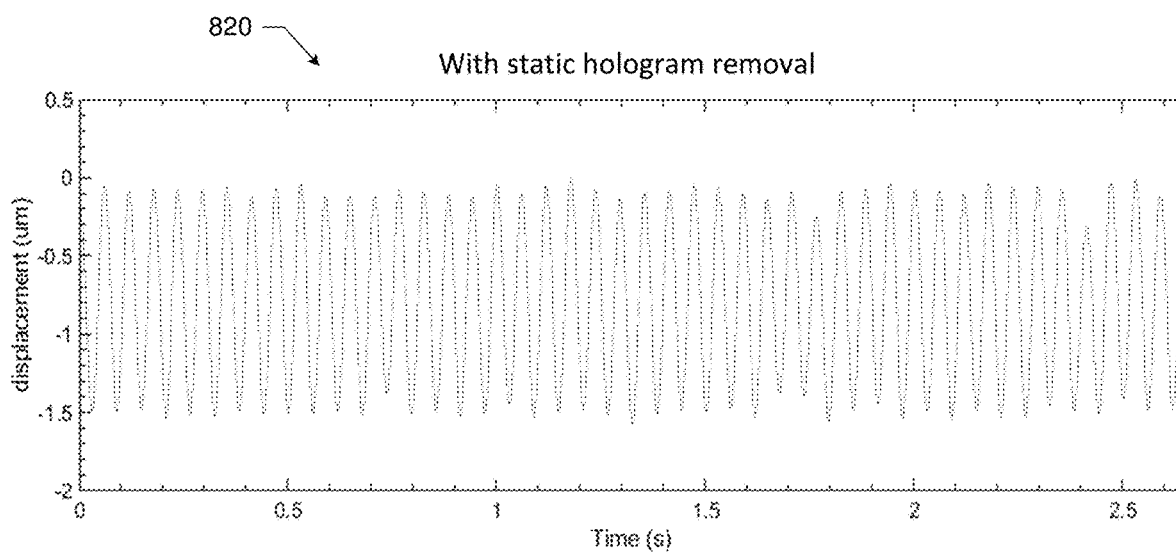
FIG. 19 illustrates an example signal response with static hologram removal performed according to some example embodiments.

The process of static hologram removal, as described herein, may operate to condition the raw holographic data prior to image data reconstruction (e.g., digital Fourier transformation). The removal of this "slow moving" data operates to further eliminate noise from the raw holographic data in a manner that permits substantially farther imaging penetration into a volume of interest that may be bounded by or in the presence of such relatively slow moving, and non-targeted features. In this regard, for example, neural imaging may be performed at deeper depths into the neural tissue because the removal of data associated with the skull increases the signal-to-noise ratio. This can be seen in FIGS. 18 and 19 according to some example embodiments, where in graph 810 of FIG. 18 no static hologram removal was performed and the signal has a relatively small displacement, while in graph 820 of FIG. 19 static hologram removal has been performed and a substantially larger signal displacement is realized.

Example Subarray Processing

With respect to image data reconstruction 720, the holographic image processing module 530 may be configured to implement a technique referred to as subarray processing 722 according to some example embodiments. In this regard, the spatial resolution of a reconstructed holographic image may be determined by a size of the imaging array 220. However, in some instances, the full imaging array may not be required to achieve sufficient spatial resolution. As such, according to some example embodiments, to leverage the availability of portions of the imaging array 220, a concept of subarrays may be utilized. In this regard, the holographic image processing module 530 may be configured to divide the data of a hologram into multiple smaller, uncorrelated subarrays or tiles. According to some example embodiments, each tile of data may be processed as a separate, individual hologram. Forming a holographic image from each of the tiles may result in the generation of multiple images of the same target. However, each of the images may have a different speckle realization.

According to some example embodiments, the subarrays or tiles may be leveraged to reduce the phase noise in a resultant, combined image. According to some example embodiments, the holographic image processing module 530 may be configured to determine the magnitude and phase of every pixel in each of the subarray images, where a pixel corresponds to an optical sensor of the imaging array 220. Pixels having low magnitude values (e.g., below a threshold magnitude value) may have very noisy phase information. As such, the phase information associated with a low magnitude value may be assigned a lower quality score. In this regard, quality scores may be assigned in association with a number of different magnitude thresholds, with each threshold having a different value. Accordingly, by assigning a quality score to the phase value of a pixel, a weight phase difference or complex cross correlation may be used to for each of the subarray calculations, resulting in more accurate phase measurements. As such, use of the subarray approach may enable enhanced suppression of phase (or object motion) noise with degradation of spatial resolution as compared to traditional spatial filtering techniques (e.g., averaging).

As such, according to some example embodiments, the holographic image processing module 530 may be configured to divide the raw holographic data (or conditioned raw holographic data if, for example, static hologram removal was performed) for a frame into a plurality of tiles. The holographic image processing module 530 may be further configured to determine a quality score for phase data of each tile based on thresholds for the magnitude data for each tile, and generate a holographic image for each tile. Subsequently, according to some example embodiments, the holographic image processing module 530 may be configured to combine holographic images for each tile based on the quality scores.

Example Decorrelation Time Quantification

According to some example embodiments, the holographic image processing module 530 may also be configured to perform decorrelation time quantification 732 as a component of complex image analysis 730. In this regard, the determination of the decorrelation time may be useful in a number of contexts, including, for example, to directly image a target 290, for example, as a decorrelation time map. The decorrelation time between images of a target may be useful for applications that require an estimate of the mechanical properties of the target since the decorrelation time is a measure of the Brownian motion of the scatterers that are being imaged. For example, materials that are softer (e.g., neural tissue) have a faster decorrelation time (~1 ms) compared to materials that are stiffer (e.g., bone) that have a slower decorrelation time (>1 s). The decorrelation time also provides information on the dynamics of the target (e.g., tissue) or blurring due to motion. For example, vascular decorrelation times are much shorter then decorrelation times of neural tissue due to blood flow. A spatial map of the decorrelation time may reveal anatomical and functional structures that could not be resolved using standard temporal aggregation of the reconstructed hologram. An estimate of the decorrelation time may also be beneficial in applications that require motion sensing of fast tissue dynamics since the decorrelation time of the tissue drives the frame rate requirement of the imaging array 220. Further, the decorrelation time may be determined separately for separate components of an image. For example, decorrelation time may be determined for each component of a grid defined with respect to the images. Alternatively or additionally, one or more training images may be captured and used to identify features and associated feature spaces within the images for separate decorrelation time determinations. Such features and feature spaces may be determined by decomposing the images based on, for example, differences in illumination or contrast that occur at boundaries, such as, for example, at the edge of a blood vessel or other images vascular feature.

Figure 20:
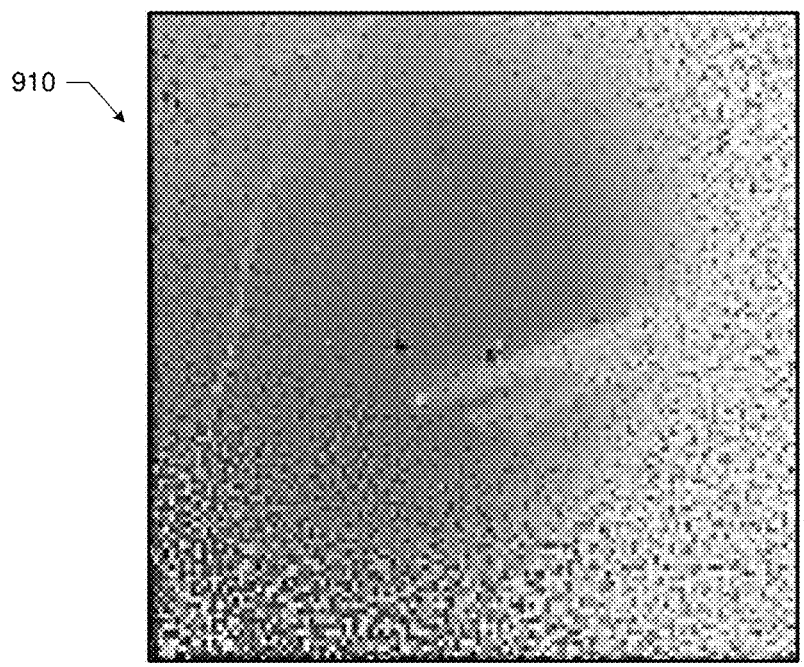
FIG. 20 illustrates an example intensity image of a target according to some example embodiments.
Figure 21:
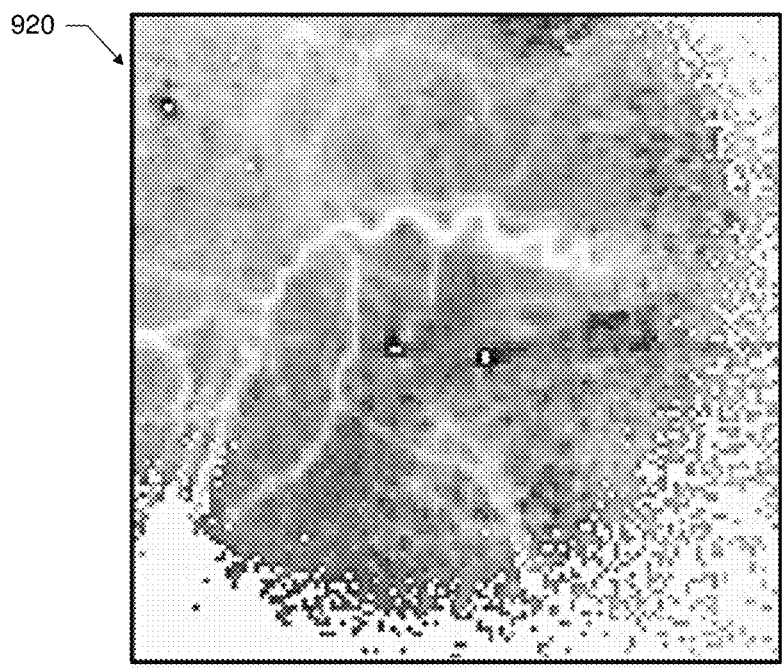
FIG. 21 illustrates an example decorrelation time image the target according to some example embodiments.

FIGS. 20 and 21 illustrate the value of the use of decorrelation time directly in imaging according to some example embodiments. In this regard, the image 910 of FIG. 20 is based on the same data as the image 920 of FIG. 21. The image 910 has been generated using intensity or magnitude as the basis for the image. In contrast, the image 920 has be generated as a spatial map of decorrelation times. As can be seen in image 920, relative to image 910, the decorrelation time as a function of spatial location can reveal deeper and more detailed features such as the vascular structure.

According to some example embodiments, the holographic image processing module 530 may be configured to determine the decorrelation time by spatially computing a full field autocorrelation function over small windows (e.g., portions of a grid) in an image. In this regard, according to some example embodiments, an image may be subdivided using a sliding window approach, where overlapping windows (e.g., in a grid) are defined with single pixel spacing. The windows may be weighted with a averaging kernel (e.g., a Gaussian kernel) to improve spatial resolution and mitigate high-frequency artifacts. As such, the decorrelation time for each pixel may be computed by determining the time at which the autocorrelation function decays to 1/exp via a fitting procedure, such as those used with respect to FIGS. 9 and 10. By determining the decorrelation time of the windows or individual pixels of the images, the decorrelation times can be spatially plotted to generate an image.

According to some example embodiments, an autocorrelation used to determine decorrelation time may be a complex autocorrelation based on phase and magnitude computed between two or more frames. For example in FIG. 9, the second data point (time=0.6 ms) is the autocorrelation value between consecutive frames, whereas the third data point (time=1.2 ms) is the autocorrelation value between every other frame. Similarly, the 4th data point in FIG. 9 is the autocorrelation value computed between every 3rd frame and so on.

An estimate of the crossing of the autocorrelation decay curve with 1/exp may be performed in a number of different ways. For example, using a non-linear fitting procedure, i.e., $f(t)=\exp(-t/A)+B$, may be one technique. In this regard, the value of A may be the decorrelation time, which may correspond to a time when the autocorrelation curve decays to 1/exp. For reference, the graph 364 in FIG. 10 has been generated using such a non-linear fitting procedure.

A cubic interpolation of the curve may be used, as shown in FIG. 9. The autocorrelation curve is interpolated when it decays to a value of 1/exp (i.e., 37%) from the baseline, i.e., $1/\exp*(1-B)+B$, where the value of B is the baseline. For example, in FIG. 9., decorrelation occurs at a autocorrelation value of 0.47 ms based on a baseline value of 0.16. The baseline of the autocorrelation decay may be accounted for in the fitting method with the value of B being the baseline.

Cubic interpolation may be used to ensure that the curve is smooth at each data point (i.e., continuous 1st order derivatives). For reference, the curve of FIG. 9 is generated using linear interpolation (not cubic) so there are discontinuities. According to the some example embodiments, the interpolation approach used may be selected to be the cubic interpolation approach since it produces very similar decorrelation values with greatly reduced computation time.

Example Complex Cross Correlation

According to some example embodiments, the holographic image processing module 530 may also be configured to perform complex cross correlation 736 as a component of complex image analysis 730. In this regard, complex cross correlation may be an improved method of computing a differential phase. Because the complex cross correlation may be determined or calculated in complex space, a continuous phase vector may be realized.

As such, according to some example embodiments, an image may be processed using information from the magnitude and phase as computed with a complex cross correlation. Examples of the type of cross-correlation that may be used, where frame-by-frame lighting or exposure change, may include, for example, zero-normalized cross-correlation (or zero-normalized cross-covariance). A computation of a differential phase in real space may involve computing a phase difference between two frames of data in real space. A drawback of such a real space approach is that the differential phase value can wrap due to a non-continuous phase jump at $+/-\pi$. To avoid this drawback, according to some example embodiments, a complex cross correlation may be utilized. As mentioned above, this discontinuity can be avoided because the differential phase calculation may be performed in complex space where the discontinuity does not exist and a continuous phase vector can be realized.

Additionally, the complex cross correlation according to some example embodiments, may carry information about magnitude correlations between two frames. The information regarding magnitude correlations may also provide information about changes in the optical scatters in the target (e.g., tissue) between the frames, which may be indicative of tissue decorrelation due to Brownian motion. As such, using the complex cross correlation, a decorrelation may be computed from a field autocorrelation function (e.g., the autocorrelation function otherwise described herein). However, the field autocorrelation function may only be directly calculated using a full complex image collected by coherent optics. In this regard, optical methods that only collect intensity or magnitude information may be limited to indirectly estimating the field autocorrelation function, and thus the tissue decorrelation, due to only collecting the magnitude information.

Accordingly, the holographic image processing module 530 may be configured to, according to some example embodiments, implement a complex cross correlation to determine a differential phase between frames. Additionally, the holographic image processing module 530 may be configured to determine a decorrelation time of a target from a field autocorrelation function based on a complex cross correlation applied to a sequence of frames.

Example Differential Phase Calculation

According to some example embodiments, the holographic image processing module 530 may also be configured to perform differential phase calculation 734 as a component of complex image analysis 730. In this regard, differential phase measurements, according to some example embodiments, may be utilized to extract relative motion (i.e., displacement) of a target by integrating the phase difference over time. As such, according to some example embodiments, the holographic image processing module 530 may be configured to determine differential phase measurements to extract indications of relative motion of the target 290. Additionally, differential phase measurements may be utilized to extract a velocity of a target 290 by computing an angle of the complex correlation vector between two frames, with the relative motion (i.e., displacement) being an integral of the velocity.

In this regard, according to some example embodiments, a complex image may be processed using differential phase calculations using different time intervals. Because, as described herein, the holographic imaging system 500 may operate at a relatively high frame rate, maximum flexibility may be provided for optimizing signal detection and the use of phase-based algorithms. According to some example embodiments, a differential phase may be determined between two subsequent images of the target, and because the measurement is a differential measurement, increasing time between frames may increase the phase difference because the target will have had more time to move. However, in some cases, such increased motion may not occur if the motion direction reverses between subsequent frames. As such, the linear increase in the signal may be offset by changes in the phase noise. Further, since phase noise increases exponentially as frame separation approaches the tissue decorrelation time, the frame rate may be selected to maximize overall signal-to-noise ratio of the desired signal of interest. Additionally, an issue with phase wrapping may be considered since the measured phase difference may not be greater than $2\pi$. If phase wrapping begins to occur, the frame rate may be increased, a longer optical wavelength of operation may be selected, or two optical wavelengths may be used to generate a synthetic wavelength longer than the optical wavelength. Further, to improve the signal-to-noise ratio, the average phase difference may be calculated over a specified region of interest (ROI) in space. Increasing the ROI size decreases phase noise at the expense of spatial resolution.

Example Digital Spatial Filtering

According to some example embodiments, the holographic image processing module 530 may also be configured to perform digital spatial filtering 738. In this regard, digital spatial filters may be applied to frames of image data to enhance the signal of interest relative to undesired noise. For example, neural activity may be commonly corrupted by noise sources such as those from blood flow (occurring at the frequency of the heart rate). The signature of this blood flow signal may be global in that the whole tissue moves up or down together due to the effect of the blood flow signal. In this regard, the signature of the signal may be defined by, for example, repeating behavior (such as that of a heartbeat to breathing) or a regular sinusoidal behavior at a certain frequency. The neural activity is then be superimposed on that global signal, e.g., the blood flow signal. Via application of the digital spatial filter, which may be implemented as a spatial high-pass filter, global motion caused by, for example, the blood flow signal, may be mitigated and removed to increasingly isolate the activity (e.g., movement) of interest (e.g., neural activity).

Example Methods of Operation—Processing

Figure 22:
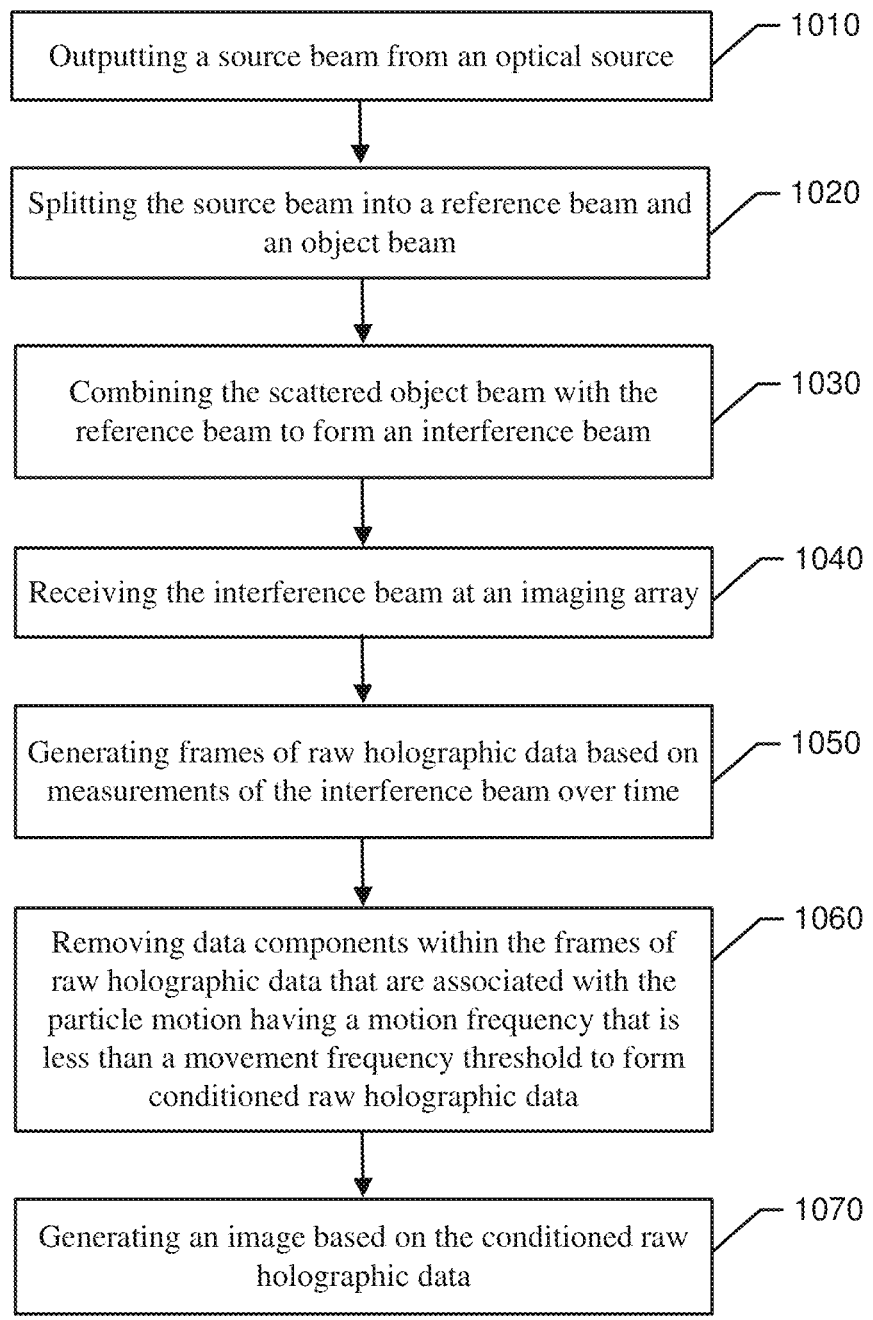
FIG. 22 illustrates a flow chart of an example method for raw holographic data image data processing according to some example embodiments.

According to some example embodiments, various methods for implementing a holographic imaging system to perform raw holographic data and image processing are provided based on the techniques described herein. In this regard, FIG. 22 illustrates a flow chart of an example method according to some example embodiments. The example method may comprise, at 1010 outputting a source beam from an optical source, and, at 1020, splitting the source beam into a reference beam and an object beam. In this regard, the object beam may be incident on a target to form a scattered object beam. The example method may further comprise, at 1030, combining the scattered object beam with the reference beam to form an interference beam, at 1040, receiving the interference beam at an imaging array, and, at 1050, generating frames of raw holographic data based on measurements of the interference beam over time. The example method may further comprise, at 1060, removing data components within the frames of raw holographic data that are associated with the particle motion having a motion frequency that is less than a movement frequency threshold to form conditioned raw holographic data, and, at 1070, generating an image based on the conditioned raw holographic data.

Additionally, according to some example embodiments, the example method may further comprise removing data components within the frames of raw holographic data that are associated with the particle motion having a frequency that is less than a movement frequency threshold (which may be a movement frequency of the target of interest) by averaging the frames of raw holographic data to form an average frame, and subtracting the data of the average frame from the raw holographic data of the one or more frames to generate the conditioned raw holographic data. Additionally or alternatively, according to some example embodiments, the example method may further comprise separating raw holographic data corresponding to a single frame of data from a single frame capture of the imaging array into a first effective frame of raw holographic data and a second effective frame of raw holographic data based on an incident angle of the interference beam on the imaging array and an incident angle of a time delayed interference beam on the imaging array. Additionally or alternatively, according to some example embodiments, generating the image may comprise dividing the conditioned raw holographic data of a frame into a plurality of tiles, determining a quality score for phase data of each tile based on thresholds for the magnitude data for each tile, generating a holographic image for each tile, and combining holographic images for each tile based on the quality scores. Additionally or alternatively, according to some example embodiments, the example method may further comprise reconstructing an image of the target and determining a decorrelation time of the target by spatially computing an autocorrelation function (e.g., a full field autocorrelation function) over small windows in the reconstructed image applied to a sequence of frames. Additionally or alternatively, according to some example embodiments, the example method may further comprise determining differential phase measurements to extract indications of relative motion of the target. Additionally or alternatively, according to some example embodiments, generating the image may comprise implementing a complex cross correlation to determine a differential phase between frames. Additionally or alternatively, according to some example embodiments, the example method may further comprise determining a decorrelation time of a target from a field autocorrelation function based on a complex cross correlation applied to a sequence of frames.

Examples of Holographic Imaging System Applications

In view of the holographic imaging systems and other example embodiments described herein, a number of new and useful applications may be realized that leverage the holographic imaging systems described herein. The following describes some non-limiting example applications of the example embodiments described herein. The example applications described below are provided in the health and healthcare space. However, it is contemplated that many applications of the technologies described herein are available outside the health and healthcare space that involve imaging and imaging analysis as provided herein. With respect to health and healthcare applications, the example embodiments may be implemented in the context of intracranial pressure, hemorrhage detection, compartment syndrome, traumatic brain injury, optical myography, neural activity—health, neural activity—brain computer interface (BCI), hydration, and anatomical imaging.

Intracranial Pressure

Example embodiments as described herein may be implemented to measure intracranial pressure. Intracranial pressure is the pressure exerted by fluids, such as cerebrospinal fluid (CSF), inside the skull and on the brain tissue. Intracranial pressure that falls outside the range of 7-15 mmHg is considered dangerous. As such, where brain injury or trauma is suspected, an accurate, non-invasive technique for taking measurements of intracranial pressure on a continuous basis is desired to track brain health in such situations.

According to various example embodiments described herein, the holographic imaging system 500 may be configured to implement such intracranial pressure measurements. In this regard, for example, the target 290 for the intracranial pressure application may be neural tissue. Via the imaging hardware and processing techniques described herein, the movement of neural tissue at the surface of the neural cortex may be measured over time to determine changes that are indicative of a change in the intracranial pressure.

An intracranial pressure implementation of the holographic imaging system 500 imaging may be performed through the skull of the patient. However, as described above, due to the static nature of the skull or other bone (relative to the neural tissue), processing of the imaging data may be performed to at least partially remove the negative contribution of the skull to the imaging data via the holographic image processing module 530 being configured to perform static hologram removal 714. Additionally, according to some example embodiments, the holographic image processing module 530 may be configured to perform sub-array processing 722 to increase the signal quality through reduction of optical phase noise of the holographic imaging system 500 to support the imaging speed needed for measuring intracranial pressure.

In this regard, to implement depth specificity and account for tissue dynamics needed for intracranial pressure measurements, the holographic imaging system 500 may include the telecentric lens 300 and spatial filter 310. Further, the array controller 225 may be configured to control the imaging array 220 to have an effective frame rate of greater than 3 kHz. The coherence length of the optical source 230 may also be 5 mm or greater. Such a configuration may support the measuring of intracranial pressure by realizing a motion sensitivity of the neural tissue at motion distances of less than 1 micrometer.

Hemorrhage Detection

Example embodiments of the holographic imaging system 500, as described herein, may be configured to perform hemorrhage detection. Hemorrhage detection may involve the detection and localization of blood pooling in targeted tissue. The holographic imaging system 500 may be configured to perform hemorrhage detection due to the differences in the mechanical properties of blood, relative to tissue, that are apparent when imaging targeted tissue. In this regard, a hemorrhage can cause increased blood flow to the location of the hemorrhage, which, in turn, causes swelling. The swelling movement of the tissue increases light scattering due to increased movement of the scatterers within the swelling tissue. This increased scattering causes decreases in the decorrelation time, thereby permitting decorrelation time to be a diagnostic for detecting a hemorrhage.

As such, to perform hemorrhage detection, the holographic imaging system 500 may be configured to perform imaging to determine differences in the mechanical properties of the targeted tissue. In the scenario where a hemorrhage may be in the brain, static hologram removal 714 may be implemented by the holographic image processing module 530. Further, in the application for hemorrhage detection, static hologram removal 714 may also be performed with respect to motion contributions due to background noise sources, for example, heartbeat. Further, since the occurrence of a hemorrhage would cause increased scattering, a threshold decrease in the decorrelation time of image frames may be used as an indication of the occurrence of a hemorrhage. As such, for hemorrhage detection the holographic image processing module 530 may be configured to perform decorrelation time quantification 732.

Also, to implement volume sensing and depth specificity for hemorrhage detection, the holographic imaging system 500 may include the telecentric lens 300 and spatial filter 310. Further, the array controller 225 may be configured to control the imaging array 220 to have an effective frame rate of greater than 3 kHz. The coherence length of the optical source 230 may also be greater than 5 mm. As indicated above, the holographic image processing module 530 may be configured to determine when the decorrelation time for the target exceeds a threshold time (i.e., a hemorrhage time threshold) thereby detecting the occurrence of a hemorrhage.

Compartment Syndrome

Example embodiments of the holographic imaging system 500, as described herein, may be configured to detect compartment syndrome. Compartment syndrome is a dangerous condition that occurs when pressure within a muscle builds to dangerous levels. Acute compartment syndrome is a medical emergency and of major concern for battlefield operations. The swelling of the muscle occurs internal to the body and can be otherwise undetectable through external evaluation. Such swelling can cause increases in internal pressures that can decrease blood flow, thereby preventing nourishment and oxygen from reaching nerves and muscle cells. Similar to a hemorrhage, the occurrence of compartment syndrome can cause swelling at or near the trauma location. The swelling movement of the tissue increases light scattering due to increased movement of the scatterers within the swelling tissue. This increased scattering causes decreases in the decorrelation time, thereby permitting decorrelation time to also be a diagnostic for compartment syndrome.

As such to perform compartment syndrome detection, the holographic imaging system 500 may be configured to perform imaging to determine differences in the mechanical properties of the targeted tissue as indicated by changes in the decorrelation time of the images of the target tissue. Detection of a threshold increase in the decorrelation time of image frames may therefore be used as an indication of the occurrence of compartment syndrome, and the holographic image processing module 530 may be configured accordingly. The holographic image processing module 530 may therefore be configured to perform decorrelation time quantification 732.

Also, for depth specificity and to ensure that imaging is being performed at a depth that can capture generalized tissue (muscle) swelling, the holographic imaging system 500 may include the telecentric lens 300 and spatial filter 310. Further, the array controller 225 may be configured to control the imaging array 220 to have an effective frame rate that is faster than 1/(the expected decorrelation time for healthy tissue of the type being targeted). The coherence length of the optical source 230 may also be less than 5 mm. As indicated above, the holographic image processing module 530 may be configured to determine when the decorrelation time for the target exceeds a threshold time (e.g. a compartment syndrome threshold time) thereby detecting the occurrence of compartment syndrome.

Traumatic Brain Injury

Example embodiments of the holographic imaging system 500, as described herein, may be configured to detect traumatic brain injury. A traumatic brain injury may involve both swelling of the neural tissue, as well as changes in neural activity in the area of the trauma. As such, the occurrence of traumatic brain injury may be indicated by both changes in the mechanical properties of the neural tissue (e.g., swelling) and changes to tissue motion (e.g., brain activity).

In this regard, for example, the target 290 for the traumatic brain injury application may be neural tissue located on the neural cortex. Via the imaging hardware and processing techniques described herein, the decorrelation time of the captured image frames and the movement of neural tissue at the surface of the neural cortex may be measured over time to determine changes that are indicative of traumatic brain injury. Imaging performed by the holographic imaging system 500 may be conducted through the skull of the patient. To account for the relative static nature of the bone of the skull, holographic image processing module 530 being configured to perform static hologram removal 714. Additionally, according to some example embodiments, the holographic image processing module 530 may be configured to perform subarray processing 722 to decrease the optical phase noise of the holographic imaging system 500 to support the imaging quality needed for measuring motion of the neural tissue indicative of neural activity.

Additionally, to detect traumatic brain injury, the holographic imaging system 500 may be configured to perform imaging to determine differences in the mechanical properties of the targeted tissue as indicated by changes in the decorrelation time of the images of the target neural tissue. Detection of a threshold increase in the decorrelation time of image frames may therefore be used as an indication of traumatic brain injury, and the holographic image processing module 530 may be configured accordingly. The holographic image processing module 530 may therefore be configured to perform decorrelation time quantification 732.

Also, to detect traumatic brain injury, spatial resolution on the order of 1 to 5 mm may be required. Additionally, volume sensing in the 1 to 5 mm, with depth specificity, may be required. Finally, motion sensitivity at 1 to 5 micrometers may also be needed. To satisfy these requirements, the holographic imaging system 500 may include the telecentric lens 300 and spatial filter 310. Further, the array controller 225 may be configured to control the imaging array 220 to have an effective frame rate that is faster than 1/(the expected decorrelation time for healthy tissue of the type being targeted). The coherence length of the optical source 230 may also be less than 5 mm. As indicated above, the holographic image processing module 530 may be configured to determine the occurrence of a traumatic brain injury by determining when the decorrelation time for the target neural tissue exceeds a threshold time (e.g., traumatic brain injury threshold time) and the changes in the motion of the neural tissue are below a threshold motion rate (e.g., traumatic brain injury motion rate threshold) that is associated with healthy neural activity.

Optical Myography

Example embodiments of the holographic imaging system 500, as described herein, may be configured to perform optical myography. Optical myography is an optical equivalent of electromyography (EMG), which evaluates and records the electrical activity produced by skeletal muscles, but is found to lack the specificity needed to control complex motion for prosthetic limb control. However, performance of optical myography by the holographic imaging system 500 may provide the needed specificity for prosthetic limb control.

In this regard, the holographic imaging system 500 may be oriented to target nerve and related tissue associated with the limb to be monitored and controlled. To detect such nerve signals, the holographic imaging system 500, and the holographic image processing module 530 may be configured to detect tissue motion of the target tissue. In this regard, the motion may be recorded and compared to movement signatures that are indicative of signals for physical movements of the limb (e.g., signatures for tapping an index finger, tapping a middle finger, or the like).

According to various example embodiments described herein, the holographic imaging system 500 may be configured to capture and detect such tissue motion by operating at a high effective frame rate. As such, according to some example embodiments, the holographic image processing module 530 may be configured to perform subarray processing 722 to decrease the effective phase noise of the holographic imaging system 500 to support the imaging quality needed for measuring such motion. Additionally, the holographic image processing module 530 may be configured to perform digital spatial filtering 738 to reduce common noise that is received across many or all of the sensors of the imaging array 220 to improve a localized signal used to detect tissue motion.

In this regard, to implement special resolution at 1 to 5 mm, volume sensing at less than 1 mm, depth specificity, and account for fast tissue dynamics (i.e., less than 50 ms) needed for optical myography, the holographic imaging system 500 may include the telecentric lens 300 and spatial filter 310. Further, the array controller 225 may be configured to control the imaging array 220 to have an effective frame rate that is faster than 1/(the expected decorrelation time for healthy tissue of the type being targeted). The coherence length of the optical source 230 may also be less than 5 mm and the optical wavelength of the optical source 230 may be relatively long. Such a configuration of the holographic imaging system 500 may permit measuring of tissue motion at distances of 1 and 5 micrometers to support optical myography.

Neural Activity—Health

Example embodiments of the holographic imaging system 500, as described herein, may be configured to detect neural activity to determine brain health. The detection of neural activity, even without high levels of spatial resolution, can be an indication of brain health by indicating that targeted neurons are capable of firing. To detect activity of the neurons, the holographic imaging system 500 may be oriented to target neural tissue on the cortex of the brain. To detect general neural activity, the holographic imaging system 500, and the holographic image processing module 530, may be configured to detect tissue motion to measure the target tissue movement. In this regard, the motion of the neural tissue may be indicative of neural activity and the health of the brain in the targeted area.

According to various example embodiments described herein, the holographic imaging system 500 may be configured to capture and detect such neural tissue motion by operating at a high effective frame rate. As such, according to some example embodiments, the holographic image processing module 530 may be configured to perform subarray processing 722 to decrease the optical phase noise of the holographic imaging system 500 to support the imaging quality needed for measuring such motion. Additionally, the holographic image processing module 530 may be configured to perform digital spatial filtering 738 to reduce common noise that is received across many or all of the sensors of the imaging array 220 to improve a localized signal used to detect tissue motion.

Imaging performed by the holographic imaging system 500 may be conducted through the skull of the patient. To account for the relative static nature of the bone of the skull, holographic image processing module 530 may be configured to perform static hologram removal 714. Additionally, according to some example embodiments, the holographic image processing module 530 may be configured to perform subarray processing 722 to decrease the optical phase noise of the holographic imaging system 500 and support the imaging speed needed for measuring motion of the neural tissue indicative of neural activity.

In this regard, to implement volume sensing at less than 3 mm, depth specificity, and account for fast tissue dynamics (i.e., less than 50 ms) needed for detection of neural activity, the holographic imaging system 500 may include the telecentric lens 300 and spatial filter 310. Further, the array controller 225 may be configured to control the imaging array 220 to have an effective frame rate that is faster than 1/(the expected decorrelation time for healthy tissue of the type being targeted). The coherence length of the optical source 230 may also be less than 5 mm and the optical wavelength of the optical source 230 may be relatively long. Such a configuration of the holographic imaging system 500 may permit measuring of tissue motion at motion distances of less than 1 micrometer to support neural activity detection.

Neural Activity—Brain Computer Interface (BCI)

Example embodiments of the holographic imaging system 500, as described herein, may be configured to detect neural activity to operate as a brain computer interface. The detection of neural activity using high levels of spatial resolution can facilitate an ability to detect areas of neural tissue that are active and compare the activity to signatures to interpret the activity. To detect neural activity, the holographic imaging system 500 may be oriented to target neural tissue on the cortex of the brain, and the holographic image processing module 530 may be configured to detect tissue motion to measure the target tissue movement which is indicative of neural activity and can be analyzed to interpret the activity (e.g., activity indicative of grasping a cup).

According to various example embodiments described herein, the holographic imaging system 500 may be configured to capture and detect such neural tissue motion by operating at a high effective frame rate. As such, according to some example embodiments, the holographic image processing module 530 may be configured to perform subarray processing 722 to decrease the optical phase noise of the holographic imaging system 500 to support the imaging quality needed for measuring such motion. Additionally, the holographic image processing module 530 may be configured to perform digital spatial filtering 738 to reduce common noise that is received across many or all of the sensors of the imaging array 220 to improve a localized signal used to detect tissue motion.

Imaging performed by the holographic imaging system 500 may be conducted through the skull of the patient. To account for the relative static nature of the bone of the skull, holographic image processing module 530 may be configured to perform static hologram removal 714. Additionally, according to some example embodiments, the holographic image processing module 530 may be configured to perform subarray processing 722 to decrease the optical phase noise of the holographic imaging system 500 to support the imaging quality needed for measuring motion of the neural tissue indicative of neural activity. Additionally, the holographic image processing module 530 may be configured to perform digital spatial filtering 738 to reduce common noise that is received across many or all of the sensors of the imaging array 220 to improve a localized signal used to detect tissue motion.

In this regard, to implement spatial resolution at less than 1 mm, volume sensing at less than 1 mm, depth specificity, and account for fast tissue dynamics (i.e., less than 50 ms) needed for detection of neural activity, the holographic imaging system 500 may include the telecentric lens 300 and spatial filter 310. Further, the array controller 225 may be configured to control the imaging array 220 to have an effective frame rate that is faster than 1/(the expected decorrelation time for healthy tissue of the type being targeted). The coherence length of the optical source 230 may also be less than 2 mm and the optical wavelength of the optical source 230 may be relatively short. Such a configuration of the holographic imaging system 500 may permit measuring of tissue motion at motion distances of less than 1 micrometer to support neural activity detection and interpretation.

Hydration

Example embodiments of the holographic imaging system 500, as described herein, may be configured to detect hydration and degrees of hydration. Relative hydration is expected to be manifested as changes in the viscoelastic properties of the tissue due to changes in the fluid levels. Since hydration has no dynamic signature over time, phase-based measurements from the imaging may not be required. However, as hydration changes, decorrelation time of successive images may also change, thereby permitting decorrelation time to be a diagnostic for hydration.

As such, to measure hydration and changes in hydration, the holographic imaging system 500 may be configured to perform imaging to determine differences in the mechanical properties of the targeted tissue as indicated by changes in the decorrelation time of the images of the target tissue. Detection of a decorrelation time as compared to a decorrelation time hydration threshold, or levels of decorrelation time hydration thresholds, may indicate a degree of hydration for the target tissue. Further, detection of a threshold increase in the decorrelation time of image frames may be used as an indication of the occurrence of a change in hydration, and the holographic image processing module 530 may be configured accordingly. The holographic image processing module 530 may therefore be configured to perform decorrelation time quantification 732. If the tissue being analyzed for hydration is neural tissue, then the imaging performed by the holographic imaging system 500 may be conducted through the skull of the patient. To account for the relative static nature of the bone of the skull, holographic image processing module 530 may be configured to perform static hologram removal 714.

Also, the holographic imaging system 500 may include the telecentric lens 300 and spatial filter 310 to be configured to detect hydration. Further, the array controller 225 may be configured to control the imaging array 220 to have an effective frame rate that is faster than 1/(the expected decorrelation time for tissue of the type being targeted). The coherence length of the optical source 230 may also be less than 5 mm and the optical wavelength of the optical source 230 may be relatively short. As indicated above, the holographic image processing module 530 may be configured to determine when the decorrelation time for the target exceeds one or more thresholds to thereby detect hydration.

Anatomical Imaging

Example embodiments of the holographic imaging system 500, as described herein, may be configured to perform anatomical imaging. Anatomical imaging refers to the ability to image differences in the viscoelastic properties of different tissues. For instance, the viscoelastic properties vary significantly between vascular structure, bone, and tissue. These differences permit an ability to achieve high-spatial (volumetric) images of the different tissue structures using non-ionizing radiation. In this regard, holographic imaging system 500 may be configured to perform anatomical imaging using decorrelation time for imaging.

As such, to perform anatomical imaging, the holographic imaging system 500 may be configured to use imaging to determine differences in the mechanical properties of the targeted tissue. In the scenario where the anatomical imaging may be of the brain (or other tissue with relatively static components), static hologram removal 714 may be implemented by the holographic image processing module 530. In this regard, in the application for anatomical imaging, static hologram removal 714 may also be performed with respect to motion contributions based on heartbeat. Further, decorrelation times of component features within an image may provide a basis for high contrast imaging, i.e., anatomical imaging. As such, for anatomical imaging, the holographic image processing module 530 may be configured to perform decorrelation time quantification 732.

Also, to implement spatial resolution of less than 1 mm, volume sensing of less than 1 mm, and depth specificity for anatomical imaging, the holographic imaging system 500 may include the telecentric lens 300 and spatial filter 310. Further, the array controller 225 may be configured to control the imaging array 220 to have an effective frame rate of faster than 1/(the expected decorrelation time for tissue of the type being targeted). The coherence length of the optical source 230 may also be less than 5 mm. As indicated above, the holographic image processing module 530 may be configured to perform anatomical imaging of the target by leveraging the decorrelation times for imaging purposes.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A holographic imaging system comprising:
   an optical source configured to output a source beam;
   a splitter configured to split the source beam into a reference beam and an object beam, the object beam being incident on a target to form a scattered object beam;
   a pre-filter comprising a telecentric lens and a spatial filter, the pre-filter being configured to receive the scattered object beam and filter diffuse light from the scattered object beam to form a filtered scattered object beam;
   a combiner configured to combine the filtered scattered object beam with the reference beam to form an interference beam; and
   an imaging array configured to receive the interference beam and generate raw holographic data based on the interference beam;
   wherein the telecentric lens is configured to magnify the scattered object beam and apply the magnified scattered object beam to the spatial filter positioned at an image plane of the telecentric lens to perform filtering to form the filtered scattered object beam;
   wherein the holographic imaging system further comprises a reference beam splitter configured to split a time delayed reference beam from the reference beam;
   wherein the imaging array is configured to receive the interference beam associated with the reference beam at a first time during a single intergration time of the imaging array and configured to receive a time delayed interference beam associated with the time delayed reference beam during the single integration time of the imaging array.

2. The holographic imaging system of claim 1, wherein the telecentric lens and the spatial filter are configured to filter light from the scattered object beam having an incident angle greater than a maximum coherent mixing angle for the holographic imaging system.

3. The holographic imaging system of claim 1 further comprising an array controller operably coupled to the imaging array to control operation of the imaging array;
   wherein the array controller is configured to control the imaging array to perform a series of frame capture events at a controlled frame rate;
   wherein, for each frame capture event, measurements of the interference beam are taken and converted into a frame of raw holographic data; and
   wherein a frame rate period based on the controlled frame rate is shorter than a decorrelation time of the target.

4. The holographic imaging system of claim 3, wherein the controlled frame rate is greater than 1000 Hertz.

5. The holographic imaging system of claim 1, wherein the reference beam is incident on the combiner at a first angle and the interference beam leaving the combiner is incident on the imaging array at a second angle;
   wherein the holographic imaging system further comprises an optical element configured to direct the time delayed reference beam at the combiner at a third angle that is different than the first angle of the reference beam to cause the time delayed interference beam leaving the combiner interference beam.

6. The holographic imaging system of claim 5, wherein raw holographic data associated with the interference beam is differentiated from raw holographic data associated with the time delayed interference beam based on the difference between the second angle of the interference beam on the imaging array and the fourth angle of the time delayed interference beam on the imaging array.

7. The holographic imaging system of claim 1, wherein the optical source is configured to output a source beam at a wavelength that causes the target to provide at least a threshold scatter level in the scattered object beam.

8. A method comprising:
   outputting a source beam from an optical source;
   splitting the source beam into a reference beam and an object beam, the object beam being incident on a target to form a scattered object beam;
   receiving the scattered object beam and filtering diffuse light from the scattered object beam via a telecentric lens and a spatial filter to form a filtered scattered object beam;
   magnifying, by the telecentric lens, the scattered object beam and applying the magnified scattered object beam to the spatial filter positioned at an image plane of the telecentric lens to perform filtering to form the filtered scattered object beam;
   combining, via a combiner, the filtered scattered object beam with the reference beam to form an interference beam;
   receiving the interference beam at an imaging array;
   splitting a time delayed reference beam from the reference beam; and
   receiving, at the imaging array, the interference beam associated with the reference beam at the first time during a single intergration time of the imaging array and receiving a time delayed interference beam associated with the time delayed reference beam during the single integration time of the imaging array.

9. The method of claim 8, further comprising filtering light from the scattered object beam, via the telecentric lens and the spatial filter, having an incident angle greater than a maximum coherent mixing angle for a holographic imaging system.

10. The method of claim 8 further comprising controlling the imaging array to perform a series of frame capture events at a controlled frame rate;
    wherein, for each frame capture event, the method further comprises capturing measurements of the interference beam and converting the measurements into a frame of raw holographic data at a time of the frame capture event; and
    wherein a frame rate period based on the controlled frame rate is shorter than a decorrelation time of the target.

11. The method of claim 10, wherein the controlled frame rate is greater than 1000 Hertz.

12. The method of claim 8 wherein the reference beam is incident on the combiner at a first angle and the interference beam leaving the combiner is incident on the imaging array at a second angle;
    wherein the method further comprises directing, via an optical element, the time delayed reference beam at the combiner at a third angle that is different than the first angle of the reference beam to cause the time delayed interference beam leaving the combiner to be incident on the imaging array at a fourth angle that is different than the second angle of the interference beam.

13. The method of claim 12, wherein raw holographic data associated with the interference beam is differentiated from raw holographic data associated with the time delayed interference beam based on the difference between the second angle of the interference beam on the imaging array and the fourth angle of the time delayed interference beam on the imaging array.

14. The method of claim 8, wherein outputting the source beam comprises outputting the source beam at a wavelength that causes the target to provide at least a threshold scatter level in the scattered object beam.

15. An apparatus comprising:
    a pre-filter comprising a telecentric lens and a spatial filter, the pre-filter being configured to receive a scattered object beam from an interaction with a target and filter diffuse light from the scattered object beam to form a filtered scattered object beam, wherein the telecentric lens is configured to magnify the scattered object beam and apply the magnified scattered object beam to the spatial filter positioned at an image plane of the telecentric lens to perform filtering to form the filtered scattered object beam;
    a combiner configured to combine the filtered scattered object beam with the reference beam to form an interference beam;
    an imaging array configured to receive the interference beam and generate raw holographic data based on the interference beam; and
    a reference beam splitter configured to split a time delayed reference beam from the reference beam;
    wherein the imaging array is configured to receive the interference beam associated with the reference beam at a first time during a single intergration time of the imaging array and configured to receive a time delayed interference beam associated with the time delayed reference beam during the single integration time of the imaging array.

16. The apparatus of claim 15, further comprising an array controller operably coupled to the imaging array to control operation of the imaging array;

wherein the array controller is configured to control the imaging array to perform a series of frame capture events at a controlled frame rate;

wherein, for each frame capture event, measurements of the interference beam are taken and converted into a frame of raw holographic data; and wherein a frame rate period based on the controlled frame rate is shorter than a decorrelation time of the target.

17. The holographic imaging system of claim 1, wherein an aperture size of the spatial filter is matched to a size of the target.

* * * * *